US009855431B2

United States Patent
Ternes et al.

(10) Patent No.: US 9,855,431 B2
(45) Date of Patent: Jan. 2, 2018

(54) SYSTEMS AND METHODS FOR MONITORING FOR NERVE DAMAGE

(71) Applicant: Cardiac Pacemakers, Inc., St. Paul, MN (US)

(72) Inventors: David J. Ternes, Roseville, MN (US); Jason J. Hamann, Blaine, MN (US); Stephen Ruble, Lino Lakes, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 382 days.

(21) Appl. No.: 13/771,964

(22) Filed: Feb. 20, 2013

(65) Prior Publication Data
US 2013/0245722 A1    Sep. 19, 2013

Related U.S. Application Data

(60) Provisional application No. 61/612,840, filed on Mar. 19, 2012.

(51) Int. Cl.
*A61N 1/00* (2006.01)
*A61N 1/372* (2006.01)
(Continued)

(52) U.S. Cl.
CPC ............ *A61N 1/372* (2013.01); *A61B 5/1107* (2013.01); *A61N 1/36053* (2013.01);
(Continued)

(58) Field of Classification Search
CPC ............ A61N 1/36114; A61N 1/36053; A61N 1/0551; A61N 1/36139; A61N 1/36142;
(Continued)

(56) References Cited

U.S. PATENT DOCUMENTS 7,551,958 B2    6/2009    Libbus et al.
7,672,725 B2    3/2010    Pastore et al.
(Continued)

FOREIGN PATENT DOCUMENTS

CN    104302354 A    1/2015
JP    2005515043 A    5/2005
(Continued)

OTHER PUBLICATIONS

Arcot-Krishnamurthy, Shanta, et al., "Systems and Methods for Using Sensed Pressure for Neuro Cardiac Therapy", U.S. Appl. No. 13/309,328, filed Dec. 1, 2011, 46 pgs.
(Continued)

*Primary Examiner* — Lindsey G Wehrheim
(74) *Attorney, Agent, or Firm* — Schwegman Lundberg & Woeesner, P.A.

(57) ABSTRACT

Various device embodiments may comprise an implantable medical device for implantation in a body and for applying neural stimulation to a neural target in the body. The device may comprise a neural stimulation electrode configured for use in stimulating the neural target, a neural stimulator configured to deliver neural stimulation through the electrode to the neural target, a sensor configured to sense a physiological response to stimulation of motor fibers at the neural target, and a controller operatively connected to the neural stimulator to control the neural stimulation and operatively connected to the sensor to receive a signal indicative of the physiological response. The controller may be configured to detect a potential neural injury and perform an action in response to the detected potential neural injury.

20 Claims, 15 Drawing Sheets

(51) Int. Cl.
*A61N 1/36* (2006.01)
*A61B 5/11* (2006.01)
*A61B 5/00* (2006.01)
*A61B 5/0488* (2006.01)
*A61B 5/053* (2006.01)

(52) U.S. Cl.
CPC ............ *A61B 5/0488* (2013.01); *A61B 5/053* (2013.01); *A61B 5/4029* (2013.01); *A61B 5/686* (2013.01); *A61B 2562/0219* (2013.01); *A61N 1/36114* (2013.01); *A61N 1/36117* (2013.01)

(58) Field of Classification Search
CPC .... A61N 1/365; A61N 1/36542; A61B 5/686; A61B 5/4029; A61B 5/0488; A61B 5/053; A61B 5/1107; A61B 2562/0219
USPC ..................................................... 607/45, 46
See application file for complete search history.

(56) References Cited

U.S. PATENT DOCUMENTS

| | | | |
|---|---|---|---|
| 7,801,603 | B2 | 9/2010 | Westlund et al. |
| 7,885,710 | B2 | 2/2011 | Sih et al. |
| 2006/0259078 | A1* | 11/2006 | Libbus ............................... 607/2 |
| 2008/0051839 | A1 | 2/2008 | Libbus et al. |
| 2008/0058874 | A1* | 3/2008 | Westlund ............. A61B 5/1104 607/2 |
| 2010/0010556 | A1* | 1/2010 | Zhao et al. ..................... 607/17 |
| 2011/0015703 | A1 | 1/2011 | Ternes et al. |
| 2011/0015704 | A1 | 1/2011 | Ternes et al. |
| 2011/0301658 | A1 | 12/2011 | Yoo et al. |
| 2012/0172741 | A1 | 7/2012 | Arcot-Krishnamurthy et al. |

FOREIGN PATENT DOCUMENTS

| | | |
|---|---|---|
| JP | 2010502275 A | 1/2010 |
| JP | 2011530348 A | 12/2011 |
| JP | 2012504467 A | 2/2012 |
| JP | 2015512285 A | 4/2015 |
| WO | WO-03061759 A1 | 7/2003 |
| WO | WO-2010017457 A1 | 2/2010 |
| WO | WO-2010039853 A1 | 4/2010 |
| WO | WO-2013141996 A1 | 9/2013 |

OTHER PUBLICATIONS

Arcot-Krishnamurthy, Shantha, et al., "Systems and Methods for Using Electrical Impedance for Neuro Cardiac Therapy", U.S. Appl. No. 13/309,320, filed Dec. 1, 2011, 49 pgs.

Hincapie Ordonez, Juan Gabriel, et al., "Automatic Neural Stimulation Titration Sweep", U.S. Appl. No. 13/155,549, filed Jun. 8, 2011, 33 pgs.

Hincapie Ordonez, Juan Gabriel, et al., "Methods and Apparatus for Controlling Neurostimulation Using Evoked Responses", U.S. Appl. No. 13/158,879, filed Jun. 9, 2011, 59 pgs.

Ordonez, Juan Gabriel Hincapie, et al., "Systems & Methods to Detect Vagus Capture", U.S. Appl. No. 61/526,568, filed Aug. 23, 2011, 68 pgs.

"International Application Serial No. PCT/US2013/026896, International Preliminary Report on Patentability dated Oct. 2, 2014", 10 pgs.

"International Application Serial No. PCT/US2013/026896, International Search Report dated May 7, 2013", 4 pgs.

"International Application Serial No. PCT/US2013/026896, Written Opinion dated May 7, 2013", 8 pgs.

"Chinese Application Serial No. 201380025689.7, Office Action dated Jun. 27, 2016", With English Translation, 18 pgs.

"Chinese Application Serial No. 201380025689.7, Office Action dated Dec. 17, 2015", With English translation, 16 pgs.

"Chinese Application Serial No. 201380025689.7, Office Action dated May 22, 2015", With English Translation, 24 pgs.

"Japanese Application Serial No. 2015-501679, Office Action dated Sep. 29, 2015", With English Translation, 8 pgs.

"Chinese Application Serial No. 201380025689.7, Response filed Mar. 1, 2016 to Office Action dated Dec. 17, 2015", (English Translation of Claims), 17 pgs.

"Chinese Application Serial No. 201380025689.7, Response filed Sep. 12, 2016 to Office Action dated Jun. 27, 2016", (English Translation of Claims), 17 pgs.

"Japanese Application Serial No. 2015-501679, Office Action dated Aug. 16, 2016", With English Translation, 10 pgs.

"Japanese Application Serial No. 2015-501679, Response filed Nov. 16, 2016 to Office Action dated Aug. 16, 2016", (English Translation of Claims), 13 pgs.

* cited by examiner

SYSTEMS AND METHODS FOR MONITORING FOR NERVE DAMAGE

CLAIM OF PRIORITY

This application claims the benefit of priority under 35 U.S.C. §119(e) of Hamann et al., U.S. Provisional Patent Application Ser. No. 61/612,870, entitled "SYSTEMS AND METHODS FOR MONITORING FOR NERVE DAMAGE", filed on Mar. 19, 2012, which is herein incorporated by reference in its entirety.

TECHNICAL FIELD

This application relates generally to medical devices and, more particularly, to systems, devices and methods for monitoring for nerve damage from neural stimulation.

BACKGROUND

Implantable Medical Devices (IMDs) have been designed or proposed to treat various conditions. For example, some IMDs are designed to treat cardiac conditions and perform functions such as pacing, cardioversion and defibrillation. Some IMDs deliver neural stimulation. By way of example and not limitation, neural stimulation has been proposed as a therapy for respiratory problems such as sleep disordered breathing, blood pressure control such as to treat hypertension, cardiac rhythm management, myocardial infarction and ischemia, heart failure (HF), epilepsy, depression, pain, migraines, eating disorders, obesity, inflammatory diseases, and movement disorders.

SUMMARY

Various device embodiments may comprise an implantable medical device for implantation in a body and for applying neural stimulation to a neural target in the body. The device may comprise a neural stimulation electrode configured for use in stimulating the neural target, a neural stimulator configured to deliver neural stimulation through the electrode to the neural target, a sensor configured to sense a physiological response to stimulation of motor fibers at the neural target, and a controller operatively connected to the neural stimulator to control the neural stimulation and operatively connected to the sensor to receive a signal indicative of the physiological response. The controller may be configured to detect a potential neural injury and perform an action in response to the detected potential neural injury. In performing the action in response to the detected potential neural injury, the controller may be configured to control the neural stimulator to modify the neural stimulation in response to the potential neural injury, or control the neural stimulator to suspend the neural stimulation in response to the potential neural injury; or initiate a communication signal to an external device or store data concerning the detected potential neural injury for later communication. The controller may respond to the potential neural injury by performing any one or any combination of two or more of these actions.

Various device embodiments may comprise an implantable medical device for implantation in a body and for applying neural stimulation to a neural target in the body. The device may comprise a neural stimulation electrode configured for use in stimulating the neural target, a neural stimulator configured to deliver neural stimulation through the electrode to the neural target, and a controller operatively connected to the neural stimulator to control the neural stimulation and configured to communicate with an external motion sensor to receive a signal indicative of sensed motion caused by stimulation of motor fibers at the neural target. The controller may be configured to detect a potential neural injury and perform an action in response to the detected neural injury. In performing the action in response to the detected neural injury the controller may be configured to control the neural stimulator to modify the neural stimulation in response to the potential neural injury, or control the neural stimulator to suspend the neural stimulation in response to the potential neural injury, or initiate a communication signal to an external device, or store data concerning the detected potential neural injury for later communication.

Various device embodiments may comprise a system for delivering vagal nerve stimulation to a vagus nerve within a cervical region of a body. The system may comprise an implantable neural stimulation electrode configured to deliver neural stimulation to the vagus nerve in the cervical region, an implantable neural stimulator configured to deliver the vagal nerve stimulation through the electrode to the vagus nerve, an implantable controller operably connected to the neural stimulator to control delivery of the vagal nerve stimulation, and an accelerometer configured to sense motion from laryngeal vibration caused by stimulation of motor fibers in the vagus nerve. The controller may be configured to receive a signal indicative of the sensed motion from the accelerometer, detect a potential neural injury to the vagus nerve and perform an action in response to the detected neural injury. In detecting the potential neural injury, the controller may be configured to perform a plurality of neural stimulation threshold tests to monitor for drift in a stimulation threshold that causes the motion sensed by the accelerometer. In performing the action in response to the detected neural injury the controller may be configured to control the neural stimulator to modify the neural stimulation in response to the potential neural injury, or control the neural stimulator to suspend the neural stimulation in response to the potential neural injury, or initiate a communication signal to an external device or store data concerning the detected potential neural injury for later communication.

Various method embodiments may comprise using an implantable medical device to deliver a neural stimulation therapy to a neural target, and detecting a potential neural injury. Detecting the potential neural injury may include sensing motion caused by stimulation of motor fibers at the neural target and detecting a drift in a stimulation threshold that causes the sensed motion. The method may include using the implantable medical device to perform an action as a programmed response to the detected neural injury, where using the implantable medical device to perform the action as the programmed response to the detected neural injury may include modifying the neural stimulation in response to the potential neural injury, or suspending the neural stimulation in response to the potential neural injury, or initiating a communication signal to an external device or storing data concerning the detected potential neural injury for later communication.

Various method embodiments may comprise using an implantable medical device to deliver a vagal nerve stimulation therapy to a cervical vagus nerve, and detecting a potential neural injury. Detecting the potential neural injury may include sensing laryngeal vibration caused by stimulation of motor fibers of the cervical vagus nerve and detecting a drift in a stimulation threshold that causes the sensed laryngeal vibration. The method may further comprise using the implantable medical device to perform an action as a programmed response to the detected neural injury. Using the implantable medical device to perform the action as the programmed response to the detected neural injury may include modifying the neural stimulation in response to the potential neural injury, or suspending the neural stimulation in response to the potential neural injury, or initiate a communication signal to an external device, or store data concerning the detected potential neural injury for later communication.

This Summary is an overview of some of the teachings of the present application and not intended to be an exclusive or exhaustive treatment of the present subject matter. Further details about the present subject matter are found in the detailed description and appended claims. The scope of the present invention is defined by the appended claims and their equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Figure 1:
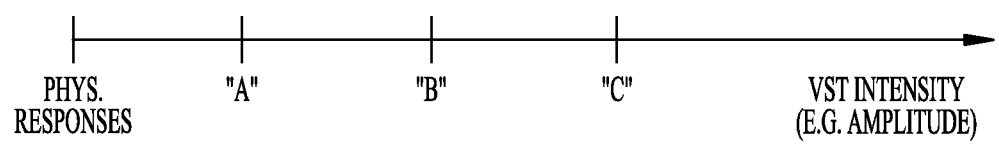
FIG. 1 illustrates increasing vagal stimulation therapy (VST) intensity from the left side to the right side of the figure, and further illustrates intensity thresholds that elicit various physiological responses to VST.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Nerve recruitment, effectiveness and neural safety depend on charge delivered and charge density (current amp×pulse width/electrode area). U.S. application Ser. No. 13/155,549, filed Jun. 8, 2011 and entitled "Automatic Neural Stimulation Titration Sweep" discusses neural stimulation safety and is incorporated herein by reference in its entirety. For example, the threshold current is reduced as the pulse width of the stimulation pulse increases. However, safety and patient tolerance for the therapy limit the charge density that can be delivered. Prolonged neural stimulation can cause damage in the peripheral/central nervous system. Thus, electrode-induced neural damage is a concern. Neural damage might occur if a device is programmed to a level of stimulation that exceeds the charge injection limit and the device has no programming restriction above the safe levels. Nerves might also be damaged by physical contact with the electrode(s).

Neural stimulation is challenging to quantify because of the time varying pattern of the stimulation waveform. By way of example and not limitation, a neural stimulation waveform could be sinusoidal or pulsatile. Current-controlled stimulation is commonly used to control the amount of charge delivered since it is not dependent on the varying tissue-electrode impedance. For example, biphasic charge-balanced pulsatile waveforms may be used to deliver neurocardiac therapy (NCT) and other neural stimulation therapies. Pulsatile waveforms are essentially periodic trains of pulses that usually have equal amplitude. There is no net direct current for these pulsatile waveforms. Direct current may cause damage to the neural tissue.

Various embodiments of the present subject matter monitor for suspected nerve damage. For example, some embodiments sense a physiological response to stimulation of motor fibers at the neural target and monitor this sensed physiological response for changes that may indicate an injury to the nerve. By way of example and not limitation, an accelerometer may be used to sense vibration or motion caused by the motor fiber vibration. If a potential neural injury is detected, some embodiments may modify the neural stimulation in response to the potential neural injury, or may suspend the neural stimulation in response to the potential neural injury, or may store data retrieved by a clinician during a device interrogation, or may provide an alert of the potential neural injury. Motor fibers do not appear to accommodate to neural stimulation. Therefore, a change in the stimulation threshold for capturing the motor fibers may indicate neural damage. Such a procedure may be used to provide an early indicator of potential nerve damage which can be used to avoid more severe nerve damage and/or promote recovery of the nerve.

Some embodiments may stimulate neural targets that include motor fibers, and monitor vibration or motion caused by stimulation of the motor fibers. By way of example and not limitation, the neural target for the stimulation may be a sciatic nerve, a peroneal nerve, a spinal motor nerve, hypoglossal nerve or a vagus nerve.

Some embodiments stimulate a vagus nerve in a cervical region of the body, and detect laryngeal vibration caused by stimulation of motor fibers in the vagus nerve. It currently appears that motor fibers innervating the larynx are the most susceptible to electrical damage when stimulating the vagus nerve. Therefore, avoiding damage to these motor fibers may avoid damage to other fibers in the vagus nerve. By way of example, and not limitation, laryngeal vibration may be detected using an accelerometer, electromyogram (EMG) signals, pressure signals, and impedance signals. Some techniques for monitoring laryngeal vibration have been disclosed in the following U.S. Patents or Patent Applications, each of which are incorporated by reference in their entirety: U.S. Pat. No. 7,801,603, filed Sep. 1, 2006 and entitled "Method and Apparatus for Vagal Nerve Stimulation Using Laryngeal Activity"," U.S. Pub. App. 20110015704, filed Jul. 13, 2010 and entitled "Physiological Vibration Detection in an Implanted Medical Device," U.S. application Ser. No. 13/309,320 filed Dec. 1, 2011 and entitled "Systems and Methods for Using Electrical Impedance for Neuro Cardiac Therapy," U.S. application Ser. No. 13/309, 328 filed Dec. 1, 2011 and entitled "Systems and Methods for Using Sensed Pressure for Neuro Cardiac Therapy," and U.S. Provisional App. No. 61/526,568 filed August 23, 201 and entitled "Systems and Methods to Detect Vagus Nerve Capture."

The vagus nerve is part of the autonomic nervous system. The autonomic nervous system (ANS) regulates "involuntary" organs, while the contraction of voluntary (skeletal) muscles is controlled by somatic motor nerves. Examples of involuntary organs include respiratory and digestive organs, and also include blood vessels and the heart. Often, the ANS functions in an involuntary, reflexive manner to regulate glands, to regulate muscles in the skin, eye, stomach, intestines and bladder, and to regulate cardiac muscle and the muscles around blood vessels, for example.

The ANS includes the sympathetic nervous system and the parasympathetic nervous system. The sympathetic nervous system is affiliated with stress and the "fight or flight response" to emergencies. Among other effects, the "fight or flight response" increases blood pressure and heart rate to increase skeletal muscle blood flow, and decreases digestion to provide the energy for "fighting or fleeing." The parasympathetic nervous system is affiliated with relaxation and the "rest and digest response" which, among other effects, decreases blood pressure and heart rate, and increases digestion to conserve energy. The ANS maintains normal internal function and works with the somatic nervous system. Afferent neurons convey impulses towards the central nervous system (CNS), and efferent neurons convey impulses away from the CNS.

Stimulating the sympathetic and parasympathetic nervous systems can cause heart rate, blood pressure and other physiological responses. For example, stimulating the sympathetic nervous system dilates the pupil, reduces saliva and mucus production, relaxes the bronchial muscle, reduces the successive waves of involuntary contraction (peristalsis) of the stomach and the motility of the stomach, increases the conversion of glycogen to glucose by the liver, decreases urine secretion by the kidneys, and relaxes the wall and closes the sphincter of the bladder. Stimulating the parasympathetic nervous system (inhibiting the sympathetic nervous system) constricts the pupil, increases saliva and mucus production, contracts the bronchial muscle, increases secretions and motility in the stomach and large intestine, increases digestion in the small intestine, increases urine secretion, and contracts the wall and relaxes the sphincter of the bladder. The functions associated with the sympathetic and parasympathetic nervous systems are many and can be complexly integrated with each other.

A reduction in parasympathetic nerve activity contributes to the development and progression of a variety of cardiovascular diseases. Some embodiments of the present subject matter can be used to prophylactically or therapeutically treat various cardiovascular diseases by modulating autonomic tone. Neural stimulation to treat cardiovascular diseases is referred to herein as neurocardiac therapy (NCT). Vagal stimulation used to treat cardiovascular diseases may be termed either vagal stimulation therapy (VST) or NCT. However, VST may be delivered for non-cardiovascular diseases, and NCT may be delivered by stimulating a nerve other than the vagal nerve, such as spinal nerves, etc. Autonomic Modulation Therapy (AMT) has been used to generally refer to neural stimulation of a neural target in the autonomic nervous system. AMT may but does not necessarily include VST, as AMT may be delivered by stimulating various parasympathetic or sympathetic targets in the body. Furthermore, AMT may but does not necessarily include NCT. Examples of cardiovascular diseases or conditions that may be treated using VST include hypertension, HF, atrial and ventricular arrhythmias and cardiac remodeling. These conditions are briefly described below.

Hypertension is a cause of heart disease and other related cardiac co-morbidities. Hypertension occurs when blood vessels constrict. As a result, the heart works harder to maintain flow at a higher blood pressure, which can contribute to HF. Hypertension generally relates to high blood pressure, such as a transitory or sustained elevation of systemic arterial blood pressure to a level that is likely to induce cardiovascular damage or other adverse consequences. Hypertension has been defined as a systolic blood pressure above 140 mm Hg or a diastolic blood pressure above 90 mm Hg. Consequences of uncontrolled hypertension include, but are not limited to, retinal vascular disease and stroke, left ventricular hypertrophy and failure, myocardial infarction, dissecting aneurysm, and renovascular disease. A large segment of the general population, as well as a large segment of patients implanted with pacemakers or defibrillators, suffer from hypertension. The long term mortality as well as the quality of life can be improved for this population if blood pressure and hypertension can be reduced. Many patients who suffer from hypertension do not respond to treatment, such as treatments related to lifestyle changes and hypertension drugs.

HF refers to a clinical syndrome in which cardiac function causes a below normal cardiac output that can fall below a level adequate to meet the metabolic demand of peripheral tissues. HF may present itself as congestive heart failure (CHF) due to the accompanying venous and pulmonary congestion. HF can be due to a variety of etiologies such as ischemic heart disease. HF patients have impaired autonomic balance, which is associated with LV dysfunction and increased mortality.

Cardiac remodeling refers to a complex remodeling process of the ventricles that involves structural, biochemical, neurohormonal, and electrophysiologic factors, which can result following a myocardial infarction (MI) or other cause of decreased cardiac output. Ventricular remodeling is triggered by a physiological compensatory mechanism that acts to increase cardiac output due to so-called backward failure which increases the diastolic filling pressure of the ventricles and thereby increases the so-called preload (i.e., the degree to which the ventricles are stretched by the volume of blood in the ventricles at the end of diastole). An increase in preload causes an increase in stroke volume during systole, a phenomena known as the Frank-Starling principle. When the ventricles are stretched due to the increased preload over a period of time, however, the ventricles become dilated. The enlargement of the ventricular volume causes increased ventricular wall stress at a given systolic pressure. Along with the increased pressure-volume work done by the ventricle, this acts as a stimulus for hypertrophy of the ventricular myocardium. The disadvantage of dilatation is the extra workload imposed on normal, residual myocardium and the increase in wall tension (Laplace's Law) which represent the stimulus for hypertrophy. If hypertrophy is not adequate to match increased tension, a vicious cycle ensues which causes further and progressive dilatation. As the heart begins to dilate, afferent baroreceptor and cardiopulmonary receptor signals are sent to the vasomotor central nervous system control center, which responds with hormonal secretion and sympathetic discharge. The combination of hemodynamic, sympathetic nervous system and hormonal alterations (such as presence or absence of angiotensin converting enzyme (ACE) activity) account for the deleterious alterations in cell structure involved in ventricular remodeling. The sustained stresses causing hypertrophy induce apoptosis (i.e., programmed cell death) of cardiac muscle cells and eventual wall thinning which causes further deterioration in cardiac function. Thus, although ventricular dilation and hypertrophy may at first be compensatory and increase cardiac output, the processes ultimately result in both systolic and diastolic dysfunction. It has been shown that the extent of ventricular remodeling is positively correlated with increased mortality in post-MI and heart failure patients.

Nerve cuffs may be used to stimulate the vagus nerve. Transvascularly stimulating the vagus nerve using electrodes in a blood vessel such as the internal jugular vein is less invasive. Another less invasive means for stimulating the vagus nerve includes stimulating the vagus nerve using electrodes placed proximate to the nerve within the carotid sheath. Monitoring for potential nerve injury is desirable, particularly in cuff electrode arrangements. Non-cuff electrode arrangements may be less likely to cause physical nerve injury. However, injury may still occur because the neural stimulation delivered to the neural target exceeds the charge injection limit. Therefore, monitoring for potential nerve injury may be desirable for both cuff and non-cuff electrode arrangements.

A branch of the vagus nerve is the recurrent laryngeal nerve, which includes motor fibers and innervates the laryngeal muscles. As mentioned previously, it currently appears that these motor fibers are the most susceptible to electrical damage when stimulating there vagus nerve. The vagus nerve is stimulated at a stimulation site more cranial than the position where the recurrent laryngeal nerve branches off of the vagus nerve. Stimulation that captures the vagus nerve at this stimulation site enhances efferent vagal nerve traffic from this position, propagating action potentials through the recurrent laryngeal nerve and causing laryngeal muscle activation. Various embodiments of the present subject matter may deliver vagal stimulation, and may monitor the stimulation threshold levels for activating the laryngeal muscles for use in detecting potential injury to the vagus nerve.

VST may include stimulation to increase vagus nerve traffic, stimulation to block or reduce vagus nerve traffic, unidirectional stimulation of the vagus nerve (e.g. stimulation that significantly affects nerve traffic in the afferent direction but not the efferent direction, or stimulation that significantly affects nerve traffic in the efferent direction but not the afferent direction), or stimulation that is non-unidirectional (e.g. stimulation that significantly affects nerve traffic in both the afferent and efferent direction). Therefore, the VST delivered from the stimulation electrodes for the therapy may enhance efferent vagal nerve traffic after vagus nerve capture is verified or the therapy is titrated. However, the present subject matter may be used to verify vagus nerve capture, and then provide a VST that does not enhance efferent vagal nerve activity. For example, the device may be configured to block efferent vagal nerve activity or to deliver VST to unidirectionally enhance afferent vagus nerve activity after vagus nerve capture is verified.

The vagus nerve is a complex physiological structure with many neural pathways that are recruited at different stimulation thresholds. Various physiological responses to vagal stimulation are associated with various thresholds of VST intensity. For example, FIG. 1 illustrates increasing VST intensity from the left side to the right side of the figure, and further illustrates intensity thresholds that elicit various physiological responses to VST. VST causes a physiological response "A" at a lower intensity than an intensity at which VST causes a physiological response "B", which occurs at a lower VST intensity than an intensity at which VST causes a physiological response "C". Stated another way, VST triggers response "A" after reaching a certain level, triggers response "B" along with response "A" after reaching a higher intensity, and triggers response "C" along with responses "A" and "B" after reaching an even higher intensity.

Physiological responses at lower VST intensities may have therapeutically-effective results for cardiovascular diseases such as HF. Lower VST intensities may also have therapeutically-effective results for other diseases. These responses mediate or provide pathways for these therapies. Examples of such responses that are beneficial for HF at the lower VST intensities include anti-inflammation, anti-sympathetic, and anti-apoptosis responses, and an increased nitric oxide (NO). Physiological responses at the higher VST intensities may not be desirable. Examples of responses to higher VST intensities that may reduce the ability of the patient to tolerate VST include, but are not limited to, reduced heart rate, prolonged AV conduction, vasodilation, and coughing. At least some of these responses may be desirable for some therapies but not desirable for other therapies. By way of example and not limitation, VST that reduces heart rate and or that prolongs AV conduction may be desirable to treat some cardiovascular diseases, but may not be desirable for other cardiovascular diseases. The intensity of the VST can be adjusted by adjusting parameter(s) of the stimulation signal. For example, the amplitude of the signal (e.g. current or voltage) can be increased to increase the intensity of the signal. Other stimulation parameter(s) can be adjusted as an alternative to or in addition to amplitude. For example, stimulation intensity can vary with the frequency of the stimulation signal (e.g. a frequency of stimulation pulses), a stimulation burst frequency (e.g. a plurality of bursts delivered at a burst frequency for initiating bursts where each burst includes a plurality of pulses), a pulse width and/or a duty cycle. Typical vagal nerve stimulation may have a signal amplitude of above 0.1-10 mA and a frequency of about 1-50 Hz.

Figure 2:
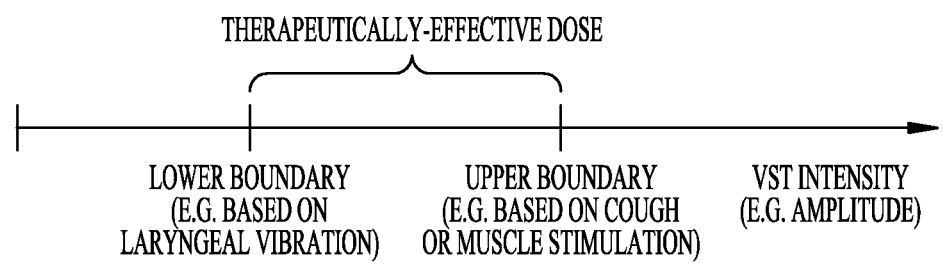
FIG. 2 illustrates increasing VST intensity from the left side to the right side of the figure, and further illustrates an intensity threshold for a laryngeal vibration response that can be used to determine capture and that can further be used as a lower boundary or to determine the lower boundary for therapy delivery.

FIG. 2 illustrates increasing VST intensity from the left side to the right side of the figure, and further illustrates an intensity threshold for a laryngeal vibration response that can be used to determine capture and that can further be used as a lower boundary or to determine the lower boundary for therapy delivery. A vagus nerve capture threshold can be set by confirming capture of the vagus nerve using laryngeal vibration. The stimulation parameters may be set based on the stimulation parameters that caused the laryngeal vibrations. For example, if the amplitude of the stimulation signal is increased to increase the VST intensity and if 1.0 mA caused laryngeal vibrations, then the pacing amplitude may be set to an offset value (x mA) above the laryngeal vibration threshold amplitude (e.g. 1 mA+x mA) or as a factor of the laryngeal vibration threshold (e.g. 1 mA*factor). Additionally, some embodiments may place an upper boundary on the VST. The upper boundary may be based on a detected undesired response to the stimulation, such as cough or undesired muscle stimulation. The vagus nerve capture threshold, as determined by sensing laryngeal vibration, may be monitored to detect changes in the threshold that may be caused by an injury to the vagus nerve.

Figure 3:
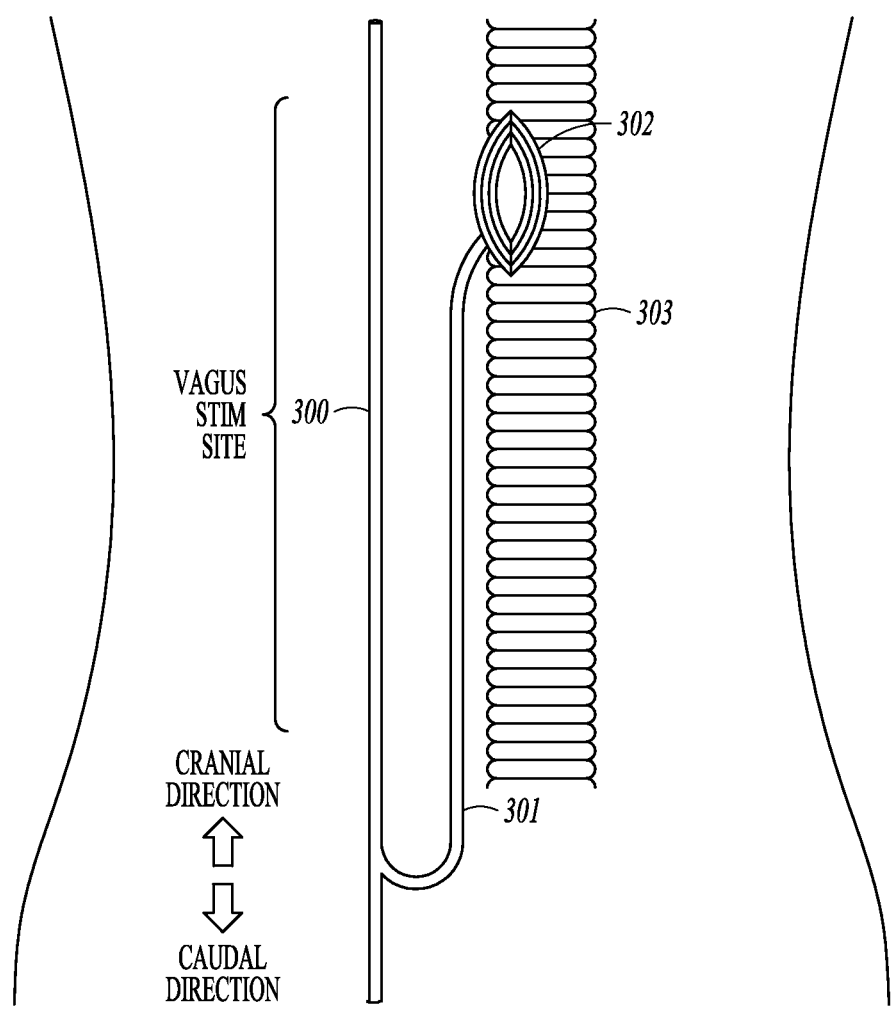
FIG. 3 generally illustrates a right vagus nerve and a recurrent laryngeal nerve branching off of the right vagus nerve to innervate the laryngeal muscles near the trachea.

FIG. 3 generally illustrates a right vagus nerve 300 and a recurrent laryngeal nerve 301 branching off of the right vagus nerve to innervate the laryngeal muscles 302 near the trachea 303. There is also a left vagus nerve (not illustrated) and a recurrent laryngeal nerve (not illustrated) branching off of the left vagus nerve to innervate the laryngeal muscles near the trachea. The recurrent laryngeal nerve branches off the vagus nerve at a position caudal to the laryngeal muscles, and then loops back cranially to innervate the laryngeal muscles. This loop is a relatively lengthy neural pathway that provides latency between the time of a vagus nerve stimulation pulse and the time of the activation of the laryngeal muscles.

The vagus nerve includes A-fibers, B-fibers, and C-fibers. A-fibers are about 5-20 µm in diameter and conduct neural responses at a rate of approximately 0.08-0.33 ms/cm. B-fibers are about 1-5 µm in diameter and conduct neural responses at a rate of approximately 0.33-1.67 ms/cm. C-fibers are about 0.2-1.5 µm in diameter and conduct neural responses at a rate of approximately 8.16-22.36 ms/cm. U.S. application Ser. No. 13/156,879, filed Jun. 9, 2011 and entitled "Methods and Apparatus for Controlling Neurostimulation Using Evoked Responses" is incorporated herein by reference in its entirety. The larger fibers have a lower stimulation threshold than smaller fibers. Thus, the A-fibers have the lowest stimulation threshold. A-fibers of the vagus nerve are also somatic fibers, some of which branch off into the recurrent laryngeal nerve that innervate the muscles of the larynx. Assuming a 0.17 ms/cm conduction rate for a 10 µm A-fiber that innervates the muscles of the larynx and assuming 50-60 cm of travel distance from the stimulated location of the vagus nerve into the recurrent laryngeal nerve and back up to the laryngeal muscles, the muscles of the larynx will activate about 8.33-10 ms after the vagus nerve is stimulated. Thus, the response of the laryngeal muscles to vagal nerve stimulation has a relatively long latency because of the relatively long travel distance. The actual distance from the stimulation site to the laryngeal muscles will depend on the location of the stimulation site and the specific anatomy of the patient. For example, taller people with longer necks may have longer recurrent laryngeal nerves. Patient specific templates may be developed to account for the specific anatomical differences in the patient.

Figure 4A:
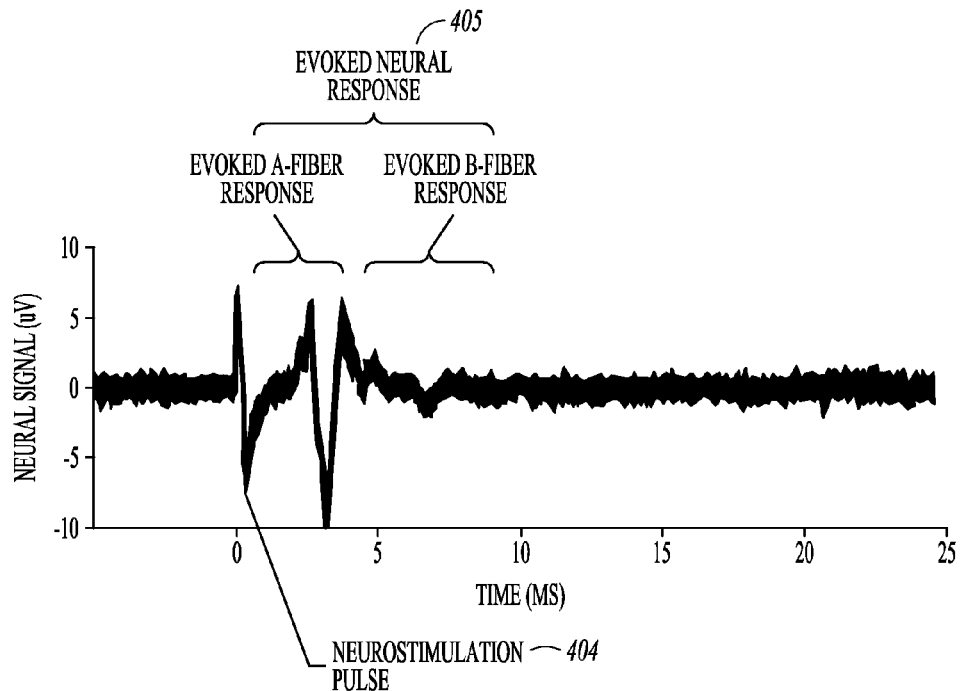
FIGS. 4A and 4B illustrate the latency of the laryngeal muscle activity to a vagus nerve pulse, comparing an ENG signal (FIG. 4A) to an EMG signal (FIG. 4B).
Figure 4B:
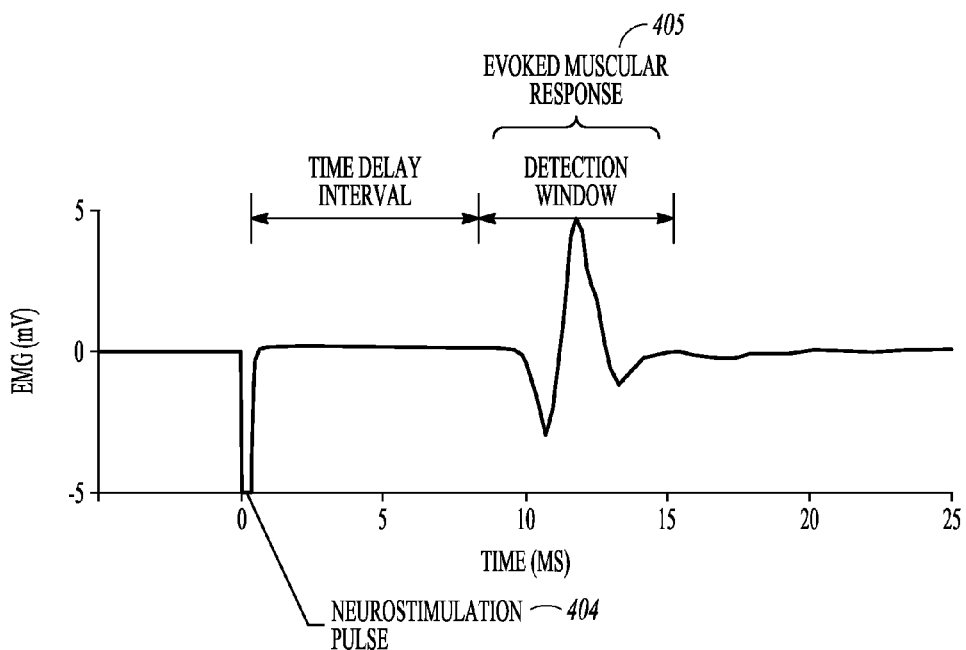

FIGS. 4A and 4B illustrate the latency of the laryngeal muscle activity to a vagus nerve pulse, comparing an ENG signal (FIG. 4A) to an EMG signal (FIG. 4B). A vagus nerve pulse 404 occurs at Time 0. An evoked neural response 405, including both an A-fiber response and a B-fiber response, to the pulse is detected by vagus ENG sensors (top) and an EMG showing the response of the laryngeal muscles to the pulse is detected by EMG sensor(s). As illustrated, the activity of the laryngeal muscles is about 10 ms after the delivery of the vagus nerve pulse. Other neural targets may have a consistent latency between the time of the neural stimulation and the muscle movement caused by conduction time within the motor fibers. Various embodiments may implement a detection window used to sense for the laryngeal activity at a time when the laryngeal activity would occur, if it occurs at all. The use of the detection window may simplify the signal processing and analysis required to discriminate the evoked muscular response.

Figure 5:
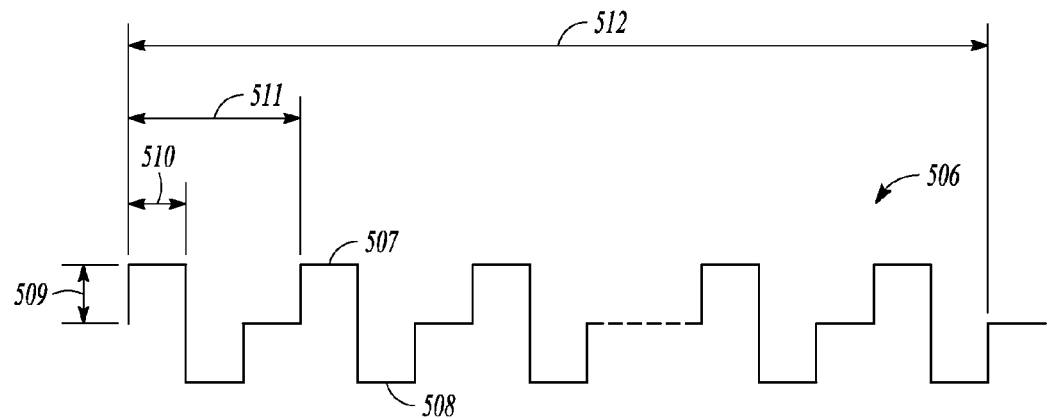
FIG. 5 illustrates biphasic current waveform, by way of example.

Various embodiments may deliver the neural stimulation using biphasic stimulation. FIG. 5 illustrates biphasic current waveform 506. A biphasic current waveform has two consecutive pulse phases that have equal charge but opposite polarity and no net DC component. These consecutive pulse phases may be referred to as a stimulating phase 507 and a reversal phase 508. The stimulating phase 507 elicits the desired physiological response such as initiation/suppression of the physiological response and the reversal phase 508 recovers the charge that was delivered during the first phase. This symmetry is intended to cause no net production of any electrolytic products in the solution. Some charge-delayed waveform embodiments provide a brief delay in the pulses. Pre-clinical studies have shown that low levels of unbalanced wave forms such as monophasic stimulation can cause vasoconstriction, thrombosis of venules and arterioles and breakdown of the blood-brain barrier within 30 seconds of stimulation (cerebral cortex of cat), but no tissue damage was found up to hours of continuous stimulation with biphasic charge balanced stimulation when the charge density was below 4.5 $\mu C/cm^2$). FIG. 5 also illustrates the amplitude 509 of the stimulating phase, a phase or pulse width 510 of the stimulating phase, the pulse period 511 of a biphasic pulse which is the inverse of the pulse frequency, and the neural stimulation burst duration 512. The neural stimulation burst comprises a train of neural stimulation pulses.

Figure 6:
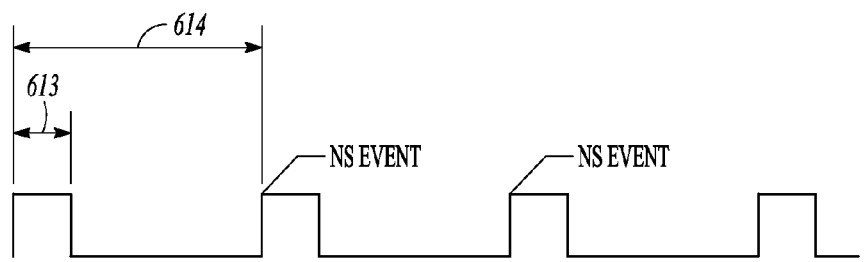
FIG. 6 illustrates a representation of intermittent neural stimulation (INS), by way of example.

Various embodiments may deliver the neural stimulation intermittently as a programmed series of stimulation ON times separated by stimulation OFF times. FIG. 6 illustrates a representation of intermittent neural stimulation (INS). The figure diagrammatically shows the time-course of a neural stimulation that alternates between intervals of stimulation being ON, when one stimulation pulse or a set of grouped stimulation pulses (i.e., a burst 613) is delivered, and intervals of stimulation being OFF, when no stimulation pulses are delivered. Thus, for example, some embodiments deliver a plurality of pulses such as the biphasic pulses illustrated in FIG. 5 for a burst duration 512 to provide a neural stimulation burst 613 illustrated in FIG. 6. The duration of the stimulation ON interval is sometimes referred to as the stimulation duration or burst duration. The start of a stimulation ON interval is a temporal reference point NS Event. The time interval between successive NS Events is the INS Interval, which is sometimes referred to as the stimulation period or burst period 614. For an application of neural stimulation to be intermittent, the stimulation duration (i.e., ON interval) must be less than the stimulation period (i.e., INS Interval) when the neural stimulation is being applied. The duration of the OFF intervals of INS are controlled by the durations of the ON interval and the INS Interval. The duration of the ON interval relative to the INS Interval (e.g., expressed as a ratio) is sometimes referred to as the duty cycle of the INS.

Figure 7:
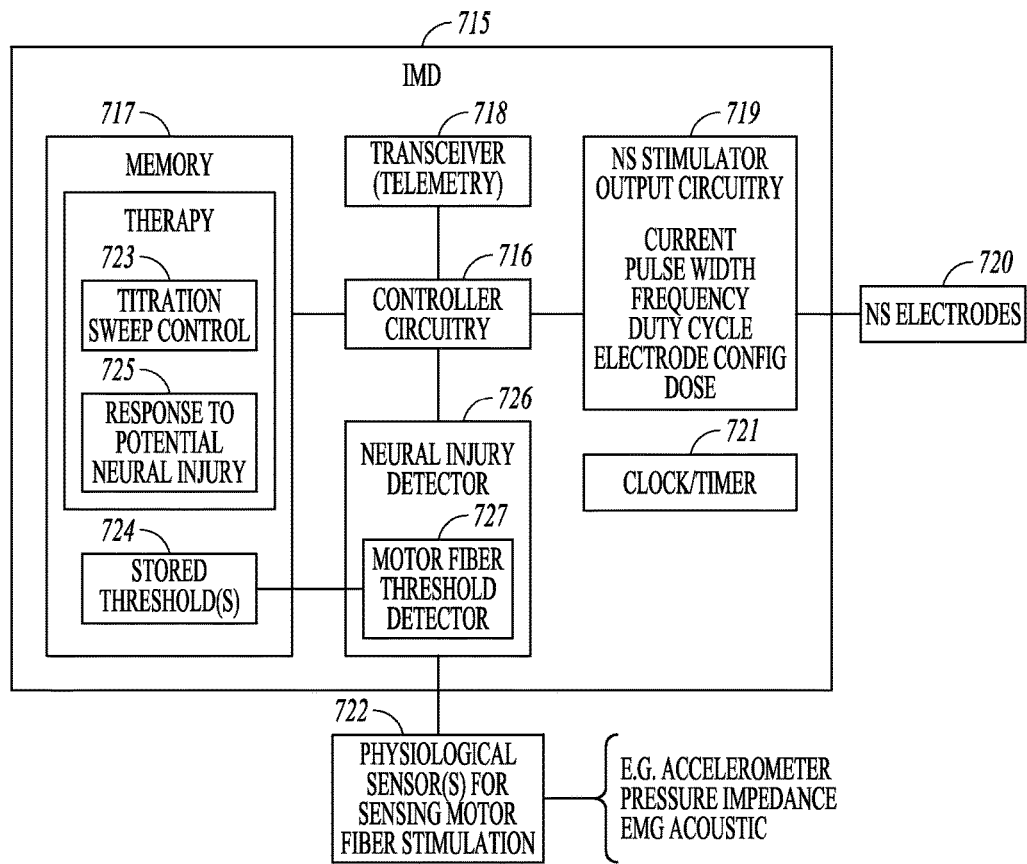
FIG. 7 illustrates, by way of example, an embodiment of a neural stimulator.

FIG. 7 illustrates, by way of example, an embodiment of a neural stimulator 715. The illustrated neural stimulator 715 provides neural stimulation signals for delivery to predetermined neural targets. The illustrated device includes controller circuitry 716 and memory 717. The controller circuitry is capable of being implemented using hardware, software, firmware or combinations thereof. For example, according to various embodiments, the controller circuitry includes a processor to perform instructions embedded in the memory to perform functions associated with the neural stimulation therapy, including instructions for performing a titration sweep for use in determining a threshold stimulation that causes capture of a motor nerve. The controller circuitry 716 may include or be integrated with other components. The illustrated device further includes a transceiver 718 and associated circuitry for use to communicate with a programmer or another external or internal device. Various embodiments have wireless communication capabilities. For example, some transceiver embodiments use a telemetry coil to wirelessly communicate with a programmer or another external or internal device. For example, some embodiments may use the transceiver 718 to communicate alerts or other information if a potential neural injury is detected. In some embodiments, the neural stimulator may be interrogated by a programmer or other external device using the transceiver, and may provide information concerning the potential neural injury during the interrogation process.

The illustrated device further includes neural stimulation output circuitry 719 which can be operably connected to the neural stimulation electrodes 720 to deliver neural stimulation to a neural target through the electrodes 720. According to some embodiments, one or more leads with NS electrodes 720 are able to be connected to the neural stimulation circuitry. Some embodiments use wireless connections between the stimulator circuitry 719 and electrodes 720. Some embodiments use transducers to provide other types of energy, such as ultrasound, light or magnetic energy.

Some embodiments are adapted to change a stimulation signal feature, the neural stimulation target and/or change the neural stimulation vector as part of a neural stimulation titration routine. The stimulation output circuitry 719 is adapted to set or adjust any one or any combination of stimulation features based on commands from the controller circuitry 716. Examples of stimulation signal features include the current amplitude, pulse width, frequency, duty cycle and dose. A clock/timer 721 may be used to implement a programmed neural stimulation schedule or to otherwise control the timing of the stimulation features. For example, a physician can program a daily schedule of therapy based on the time of day. A stimulation session can begin at a first programmed time, and can end at a second programmed time. Various embodiments initiate and/or terminate a stimulation session based on a signal triggered by a user. Various embodiments use sensed data to enable and/or disable a stimulation session. In some embodiments, the controller circuitry 716 is programmed to control the neural stimulation delivered by the stimulation output circuitry 719 according to stimulation instructions, such as a stimulation schedule, stored in the memory 717. Neural stimulation can be delivered in a stimulation burst, which is a train of stimulation pulses at a predetermined frequency. Stimulation bursts can be characterized by burst durations and burst intervals. A burst duration is the length of time that a burst lasts. A burst interval can be identified by the time between the start of successive bursts. A programmed pattern of bursts can include any combination of burst durations and burst intervals. A simple burst pattern with one burst duration and burst interval can continue periodically for a programmed period or can follow a more complicated schedule. The programmed pattern of bursts can be composed of multiple burst durations and burst interval sequences. The programmed pattern of bursts can be characterized by a duty cycle, which refers to a repeating cycle of neural stimulation ON for a fixed time and neural stimulation OFF for a fixed time.

The illustrated system may include physiological sensor(s) 722 for sensing motor fiber stimulation, which can be used in the processes of detecting a potential neural injury. Examples of such physiological sensors include, but are not limited to, an accelerometer, a pressure sensor, impedance sensor, an EMG sensor, and an acoustic sensor. The illustrated memory 717 includes instructions 723, operable on by the controller circuitry 716, to deliver the titration sweep control used to adjust the intensity of the stimulation for detecting the threshold stimulation for the motor nerve, a queue or other memory storage 724 to store threshold(s), and instructions 725, operable on by the controller circuitry 716, to respond to a potential neural injury. A neural injury detector 726, which may be incorporated as part of the controller circuitry 716, may include a motor fiber threshold detector 727 configured to perform the processes to detect the stimulation thresholds for stimulating the motor nerve, for storing and detecting changes in the thresholds to detect potential neural injuries, and responding to a potential neural injury.

Figure 8:
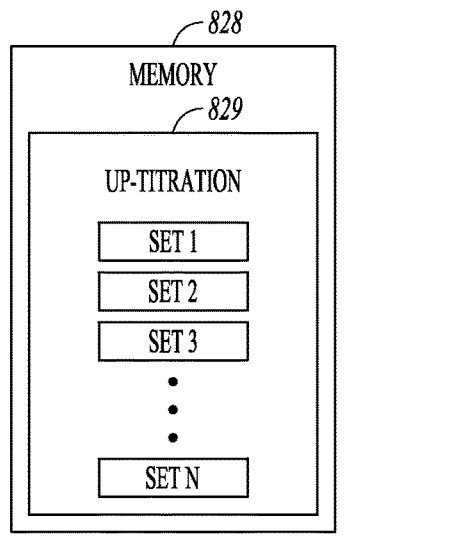
FIG. 8 illustrates a memory, according to various embodiments, that includes instructions, operable on by the stimulation control circuitry, to control an up-titration routine by progressively stepping up through defined parameter sets (e.g. parameter set 1 through parameter set N), where each set incrementally changes (increases or decreases) the stimulation dose or intensity of the stimulation.

FIG. 8 illustrates a memory 828, according to various embodiments, that includes instructions 829, operable on by the stimulation control circuitry, to control an up-titration routine by progressively stepping up through defined parameter sets (e.g. parameter set 1 through parameter set N), where each set incrementally changes (increases or decreases) the stimulation dose or intensity of the stimulation. This memory may be illustrated as part of memory 717 in FIG. 7. The memory may include a plurality of neural stimulation parameter sets, where each set includes a unique combination of parameter values for the neural stimulation and wherein each unique combination of parameter values provides neural stimulation therapy at an intensity level. The instructions include instructions for stepping through the plurality of neural stimulation parameter sets according to a schedule to change (e.g. increase) the intensity of the stimulation until the stimulation captures the motor fiber. Some embodiments may implement a down-titration routine instead of or in addition to the up-titration routine.

Figure 9:
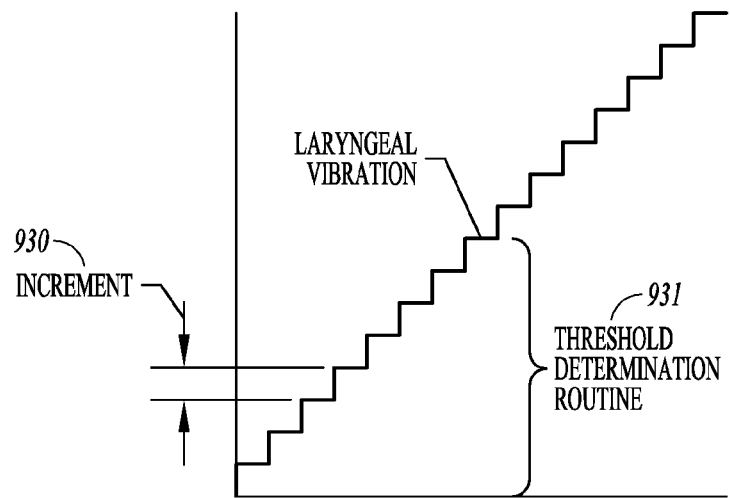
FIG. 9 illustrates an embodiment, by way of example, of a routine for finding threshold values for each of the electrode configurations.

FIG. 9 illustrates an embodiment of a routine for finding threshold values for each of the electrode configurations. The illustrated routine increases the intensity of the neural stimulation therapy over a period of time. The intensity is increased in increments 930. In the illustrated embodiments, a threshold determination routine 931 is performed to detect a laryngeal vibration response. In various embodiments, a side effect detection routine may be performed to detect an upper boundary physiologic response (e.g. cough) to the neural stimulation. Some embodiments decrease the intensity of the NCT therapy over a period of time to detect the desired or undesired physiologic responses to the neural stimulation.

Figure 10:
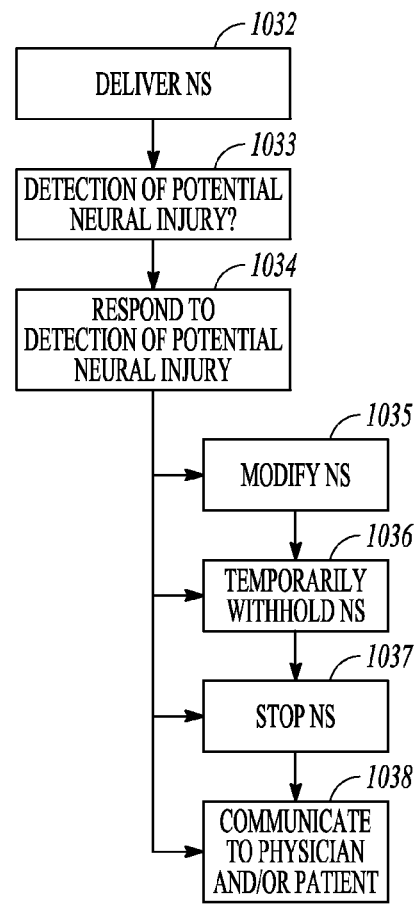
FIG. 10 illustrates an embodiment, by way of example, of a routine for detecting and responding to a potential neural injury.

FIG. 10 illustrates an embodiment of a routine for detecting and responding to a potential neural injury. The routine may be automatically performed within an implanted neural stimulator, for example. At 1032, the neural stimulation is delivered. For example, the neural stimulation may be delivered as part of a chronic neural stimulation such as an NCT (e.g. a heart failure or hypertension therapy or other NCT). At 1033, a process is performed to detect if there is a potential neural injury. The process may be implemented based on a command from a clinician, based on a command from a patient, based on results of a device interrogation, based on sensed or delivered events, or based on a programmed schedule. At 1034, the device responds to the potential neural injury. For example, the device may modify the neural stimulation 1035 either indefinitely until another event or command changes the neural stimulation back or temporarily for a defined period of time, may temporarily withhold neural stimulation 1036, may stop neural stimulation 1037, may communicate an alert or other message to a physician or other clinician, and/or to the patient 1038, or may perform various combinations of two or more of the responses 1305, 1036, 1037 or 1038. For example, the neural stimulation therapy may be automatically adjusted. In some embodiments, the response includes a communication that provides guidance to the physician.

Figure 11:
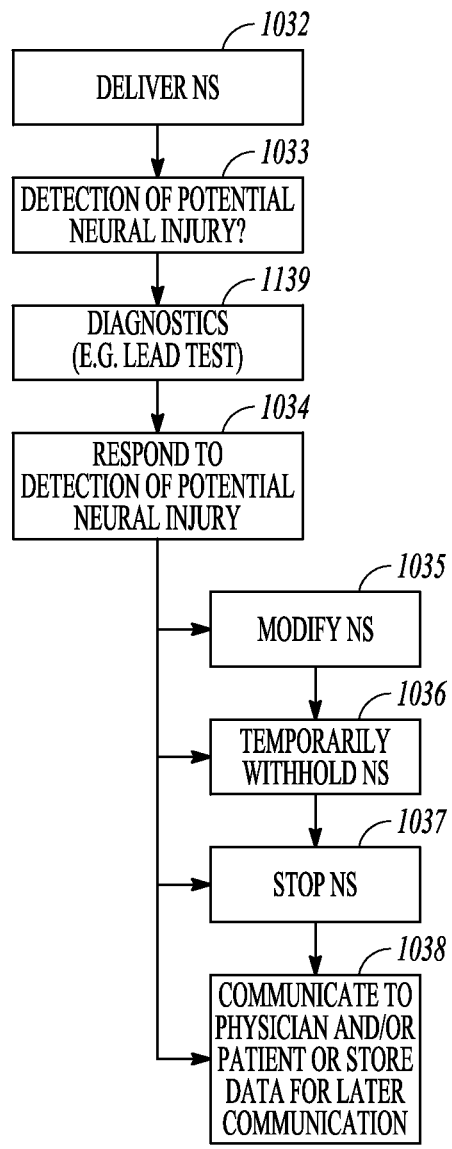
FIG. 11 illustrates an embodiment, by way of example, of a routine for detecting and responding to a potential neural injury, in which the device performs diagnostics in response to the detection of a potential nerve injury.

FIG. 11 illustrates an embodiment of a routine or detecting and responding to a potential neural injury, in which the device performs diagnostics 1139 in response to the detection of a potential nerve injury. The routine illustrated in FIG. 11 is similar to the routine illustrated in FIG. 10. For example, some embodiments perform a lead test, such as a lead impedance test, that may detect lead migration or another problem with the lead. Some diagnostics may involve monitoring therapy feedback for the neural stimulation. For example, heart rate, blood pressure, respiration or other physiological feedback may be used to monitor the effects of stimulating a vagus nerve. Because neural injury may first appear in the motor fibers of the vagus nerve, the early stages of neural injury may show a change in stimulation threshold for laryngeal vibration, but still show that the desired autonomic neural response is obtained with the neural stimulation. Therefore, if the laryngeal vibration threshold has drifted higher, but the vagal nerve stimulation still appears to be effective, then the device may indicate that an early stage neural injury is suspected. In some embodiments, the diagnostics is performed before other responses to the detection of the neural injury. In some embodiments, the diagnostics are performed during or after the other response(s) to the detection of the neural injury. A clinician may further investigate the potential neural injury by imaging the leads to determine if the lead may be malfunctioning.

Figure 12:
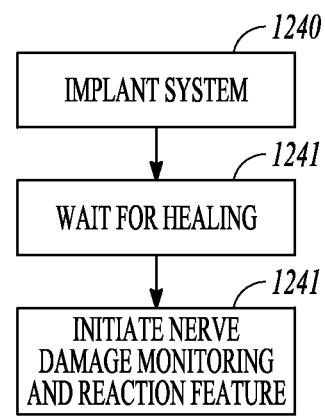
FIG. 12 illustrates an embodiment, by way of example, of a routine to monitor for nerve damage after implantation.

A procedure for implanting a neural stimulator may involve a mechanical manipulation of a nerve targeted for stimulation, which may temporarily damage the nerve. FIG. 12 illustrates an embodiment of a routine to monitor for nerve damage after implantation. For example, the implantable device may be implanted at 1240. After the implantation, the nerve damage detection process waits for a determined period of time for healing 1241 after the implantation process, and then initiates the nerve damage monitoring and reaction feature 1242. In some embodiments, the determined period of time for healing may be a default time initiated automatically to a time of implant. By way of example and not limitation, the default time may be initiated at lead insertion or first interrogation or first programming. In some embodiments, the determined period of time for healing may be a default time initiated by medical personnel or company representative at implant. In some embodiments, the determined period of time for healing may be a programmable time selected by medical personnel or company representative. In some embodiments, the determined period of time for healing may be based on a "go" command given by medical personnel at a follow-up session. In some embodiments, assuming the therapy is OFF during healing period until first follow-up, the determined period of time for healing may be the first time the amplitude is permanently programmed to something other than zero.

Figure 13:
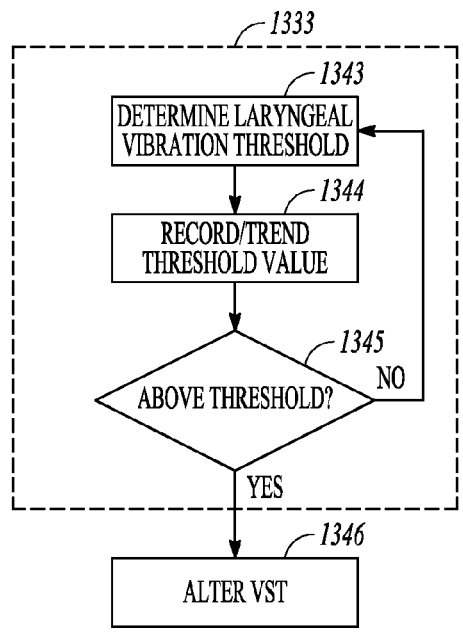
FIG. 13 illustrates an embodiment, by way of example, of a routine to monitor for nerve damage and respond by altering the stimulation parameters.

FIG. 13 illustrates an embodiment of a routine to monitor for nerve damage and respond by altering the stimulation parameters. For example, the illustrated routine may be a specific embodiment of elements 1033, 1034 and 1035 for the routine illustrated in FIG. 10. The routine illustrated in FIG. 13 detects a neural injury at 1333, which may include determining a laryngeal vibration threshold 1343, recording and trending the laryngeal vibration threshold value 1344, and determining if the laryngeal vibration threshold value, or a change in the laryngeal vibration threshold, is above a threshold 1345. At 1346, the VST is altered. In detecting a neural injury, some embodiments may detect a rate of change in the laryngeal vibration threshold. For example a rate of change higher than a defined rate may be used to identify a potential for a more serious neural injury. There may be multiple tiers of defined rates, where each rate is associated with a defined action or set of actions. These action(s) may be automatically performed in response to the detected rate of change in the laryngeal threshold. In detecting a neural injury, some embodiments may monitor for an acute change. For example, monitoring for an acute change may include monitoring for a detected change in threshold values in a short time period on the order of minutes to hours. In detecting a neural injury, some embodiments may monitor for a chronic change. For example, monitoring for a chronic change may include monitoring for a detected change in threshold values in a longer time period on the order of days or weeks. The defined level for acute changes may be lower than the defined level for chronic changes. By way of example, some embodiments may monitor for an acute change and perform an action in response to the monitored activity reaching a first level (e.g. greater than 20%). Some embodiments may monitor for a chronic change and perform an action in response to the monitored activity reaching a second level (e.g. greater than 40%).

Figure 14:
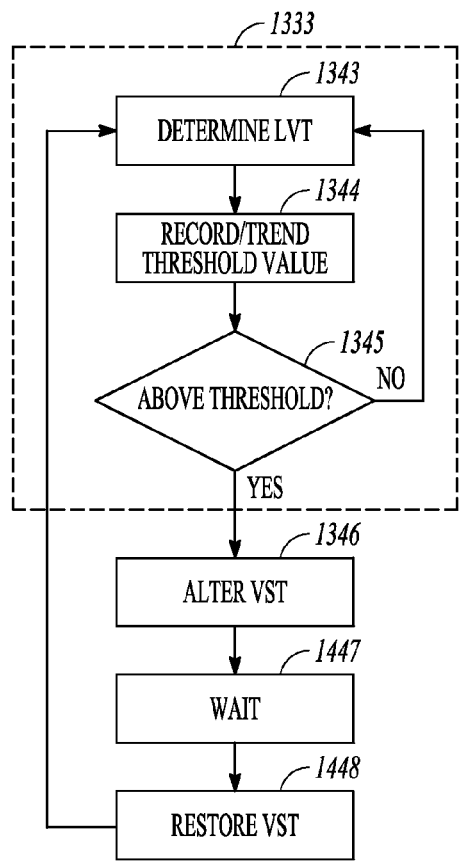
FIG. 14 illustrates an embodiment, by way of example, of a routine to monitor for nerve damage and respond by altering the stimulation parameters.

FIG. 14 illustrates an embodiment of a routine to monitor for nerve damage and respond by altering the stimulation parameters. For example, the illustrated routine may be a specific embodiment of elements 1033, 1034 and 1035 for the routine illustrated in FIG. 10. The routine illustrated in FIG. 14 is similar to the routine illustrated in FIG. 13. However, after the VST is altered at 1346 the routine illustrated in FIG. 14 waits for a defined period 1447, restores the VST intensity to the previous level 1448 or otherwise increase the VST intensity toward the previous level, and then continues to detect for neural injury 1333. The defined period 1447 may be defined based on time, or based on neural stimulation counts, or based on sensed events or based on contextual conditions, or various combinations thereof. According to some embodiments, if the potential neural injury is redetected after reinitiating delivery of the neural stimulation, then the neural stimulation may be suspended for a second period of time greater than the first period of time if the potential neural injury is redetected to provide more time for nerve recovery.

Figure 15:
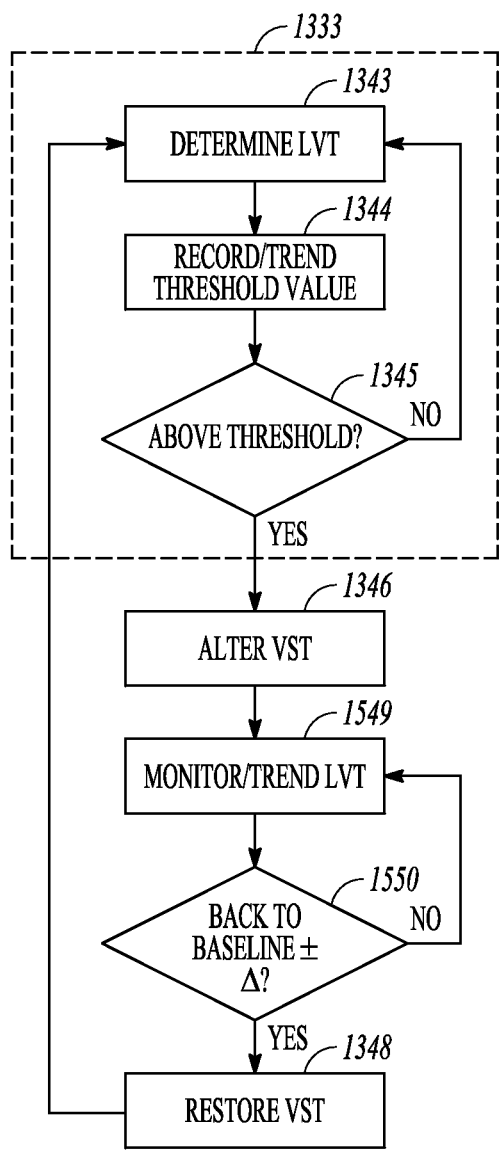
FIG. 15 illustrates an embodiment, by way of example, of a routine to monitor for nerve damage and respond by altering the stimulation parameters and monitoring the results for altering the stimulation parameters.

FIG. 15 illustrates an embodiment of a routine to monitor for nerve damage and respond by altering the stimulation parameters and monitoring the results for altering the stimulation parameters. The routine illustrated in FIG. 15 is similar to the routine illustrated in FIG. 13. However, after the VST is altered at 1346 the routine illustrated in FIG. 15 continues to monitor the laryngeal vibration threshold and trend 1549 to detect changes in the laryngeal vibration threshold. If the monitored laryngeal vibration threshold returns back to an acceptable threshold value 1550, then some embodiments restore the VST to the previous level or other increases the VST intensity toward the previous level.

Figure 16:
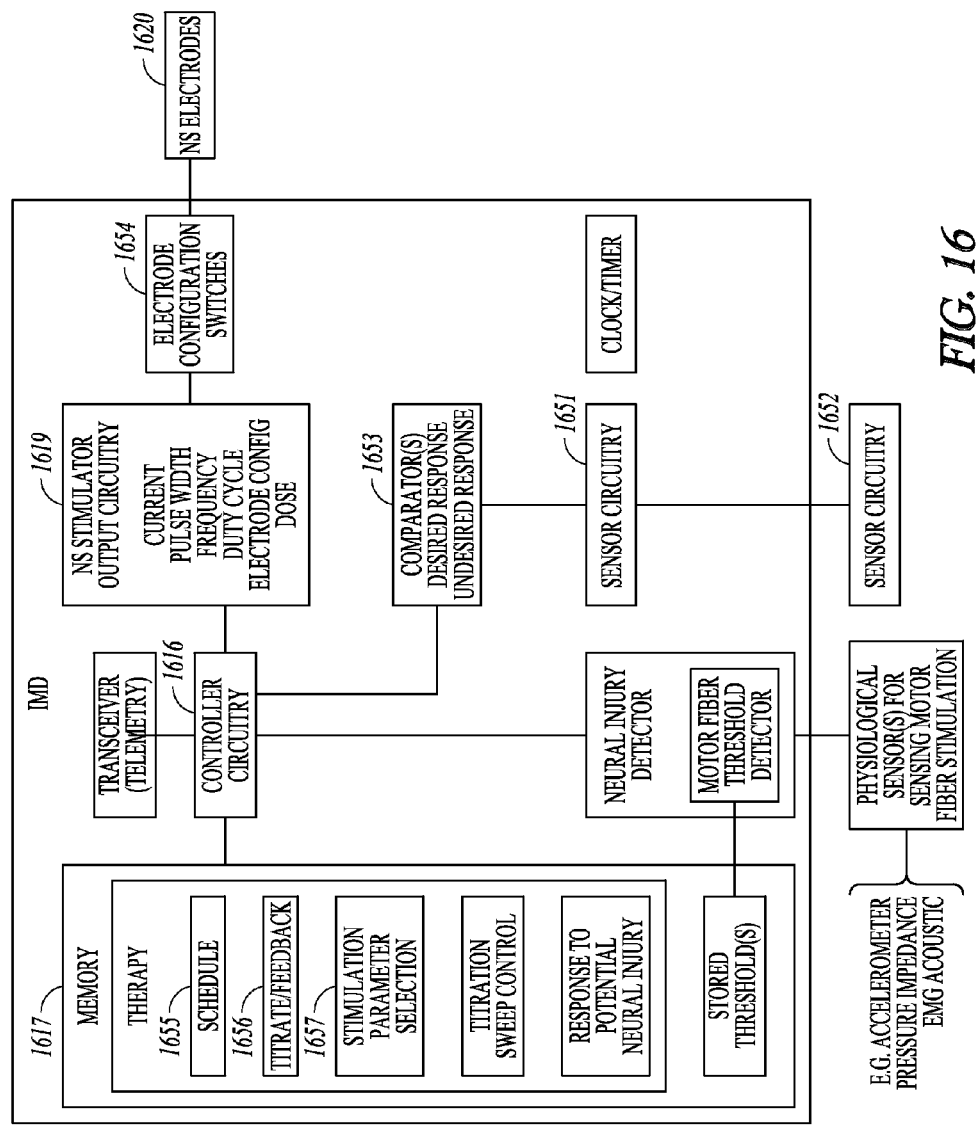
FIG. 16 illustrates an embodiment, by way of example, similar to the embodiment illustrated in FIG. 7, that includes additional physiological sensors to provide closed loop feedback control useful for converging on a desired physiological response and/or to provide feedback useful for avoiding undesired responses (e.g. "side effects") to the neural stimulation.

Various embodiments of the routines discussed above may be initiated by a clinician within a clinical setting, may be automatically initiated periodically (e.g. daily or weekly) or according to another programmed schedule, may be triggered by a patient or clinician when the patient is ambulatory away from the clinical setting, or may be triggered by a sensed even or a contextual event FIG. 16 illustrates an embodiment, similar to the embodiment illustrated in FIG. 7, but that includes additional physiological sensors to provide closed loop feedback control useful for converging on a desired physiological response and/or to provide feedback useful for avoiding undesired responses (e.g. "side effects") to the neural stimulation. The sensor circuitry 1651 and sensor(s) 1652 are used to detect a physiological response. The detected physiological responses may be physiological responses to AMT, such as cardiac activity or surrogates of cardiac activity such as blood pressure and respiration measurements. Examples of physiological responses include cardiac activity such as heart rate, HRV, PR interval, T-wave velocity, and action potential duration. Some embodiments monitor hemodynamic responses such as blood pressure, and some embodiments monitor respiratory responses such as tidal volume and minute ventilation. The monitored physiologic variables are selected to monitor effects of the neural stimulation. For example, the stimulation of an autonomic neural target such as the vagus nerve or a branch thereof may affect heart rate, blood pressure and respiration. A comparator 1653 compares the sensed physiological response to a target range stored in the memory, and the controller circuitry 1616 receives a comparison result and controls the neural stimulation based on the comparison in an attempt to keep the response within the target range. In some embodiments, the function of the comparator is performed within the controller circuitry. The target range stored in the memory can be programmable. Some embodiments use more than one feedback. For example, some embodiments require a change in one parameter, and require no change or a change within limits in another parameter. Some embodiments are adapted to change electrode configuration as part of the neural stimulation titration routine. The illustrated embodiment includes electrode configuration switches 1654, and the switches are configured to deliver neural stimulation from the output circuitry 1619 to selected neural stimulation electrodes 1620. In the illustrated embodiment, the neural stimulation output circuitry 1619 is configured to control the switches 1654 to provide the desired electrode configuration. In some embodiments, the controller circuitry 1616 is configured to control the switches 1654. The illustrated memory 1617 may further include a programmed schedule 1655 or schedules used to deliver the neural stimulation therapy and/or to perform a routine to detect suspected neural injury, instructions 1656 for use to titrate the therapy in response to sensed physiological feedback, instructions 1657 for selecting stimulation parameters. Some embodiments may be configured to respond to a suspected neural injury by switching between or among other electrode configurations.

Figure 17:
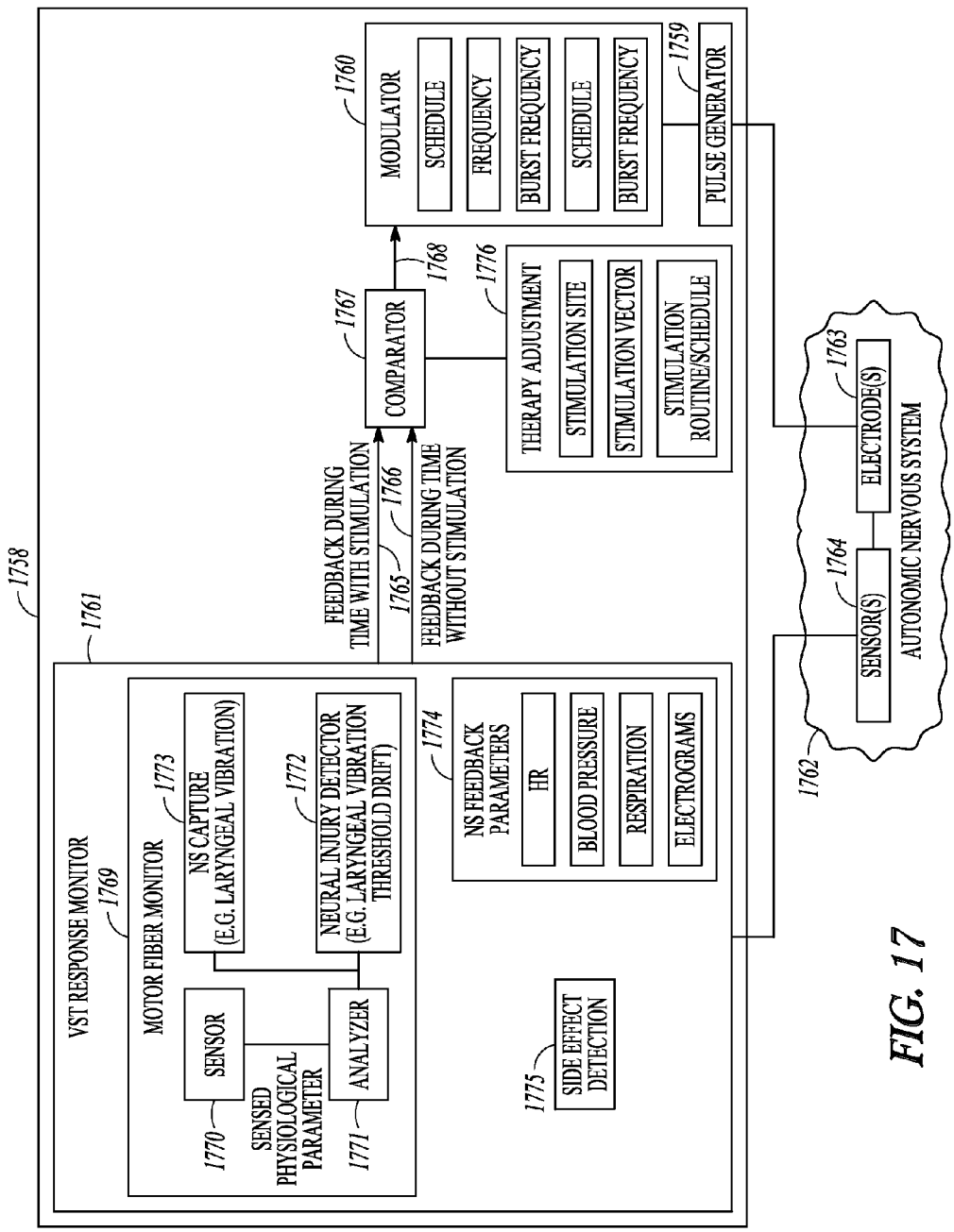
FIG. 17 illustrates, by way of example, a VST system according to various embodiments.

FIG. 17 illustrates a VST system, according to various embodiments. An implantable device may provide the entire VST system. Some embodiments use external devices to provide the monitoring functions, such as during implantation of an implantable vagus nerve stimulator, or such as during a patient-initiated or clinician-initiated process. Some embodiments use implanted leads and external stimulators. The illustrated VST system 1758 includes a pulse generator 1759 to provide VST, a modulator 1760 to change or modulate intensity of the VST, and a VST response monitor 1761 to provide feedback. The autonomic nervous system is generally illustrated at 1762. Appropriate electrode(s) 1763 are used to provide desired neural stimulation and sensor(s) 1764 to sense a parameter that is affected by the neural stimulation. Physiological parameter(s) that quickly respond to VST can be used in closed loop systems or during the implantation process. Examples of such parameters include heart rate, laryngeal vibrations, blood pressure, respiration, and electrogram parameters. The present subject uses a strain gauge or pressure sensor to detect laryngeal vibrations or cough caused by the stimulation. Other cardiovascular parameter(s) and other surrogate parameters that have a quick and predictable response indicative of the overall response of the parasympathetic nervous system to the neural stimulation can be used. Other parameter(s) that have a slower response may be used to confirm that a therapeutically-effective dose is being delivered. The sensor(s) and electrode(s) can be integrated on a single lead or can use multiple leads. Additionally, various system embodiments implement the functions using an implantable neural stimulator capable of communicating with a distinct or integrated implantable cardiac rhythm management device.

The illustrated response monitor 1761 monitors the parameter during a time with stimulation to provide a first feedback signal 1765 indicative of a parameter value corresponding to a time with stimulation and during a time without stimulation to provide a second feedback signal 1766 indicative of a parameter value corresponding to a time without stimulation. The signals 1765 and 1766 are illustrated as separate lines. These signals 1765 and 1766 can be sent over different signal paths or over the same signal path. A comparator 1767 receives the first and second feedback signals 1765 and 1766 and determines a detected change in the parameter value based on these signals. Additionally, the comparator compares the detected change with an allowed change, which can be programmed into the device. For example, the device can be programmed to allow a heart rate reduction during VST to be no less than a percentage (e.g. on the order of 95%) of heart rate without stimulation. The device may be programmed with a quantitative value to allow a heart rate reduction during VST to be no less than that quantitative value (e.g. 5 beats per minute) of heart rate without stimulation. The comparator 1767 can provide a comparison result 1768, which is used to appropriately control the modulator to adjust the applied VST.

The VST response monitor may include a motor fiber monitor 1769. The motor fiber monitor 1769 may include a sensor 1770 and an analyzer 1771. The analyzer analyzes a plurality of sensed signals. Some embodiments may analyze the signal from the sensor to detect a suspected neural injury 1772 (e.g. detect laryngeal vibration threshold drift to detect suspected vagus nerve injury). Some embodiments may analyze the signal from the sensor confirm capture of the nerve 1773 (e.g. confirm laryngeal vibration to confirm capture of the vagus nerve). Some embodiments use a therapy protocol that adjusts the VST intensity. The VST intensity may be adjusted based on feedback parameters 1774 such as heart rate, blood pressure, respiration, and electrogram measurement. The VST response monitor 1769 may also monitor for side effect 1775, such as cough, muscle twitch, or other undesired response to the VST.

Various modulator embodiments adjust VST intensity by changing an amplitude of a stimulation signal used to provide VST, by changing a frequency of a stimulation signal used to provide VST, by changing a burst frequency of a stimulation signal used to provide VST, by changing a pulse width of a stimulation signal used to provide VST, by changing a duty cycle of a stimulation signal used to provide VST, or various combinations of two or more of these stimulation signal characteristics. Some embodiments may include a therapy adjustment module 1776, which may be used to adjust a stimulation site for delivering the neural stimulation, adjust a stimulation vector, or adjust a stimulation routine or schedule. These adjustments may be made in response to detection of a suspected neural injury in an effort to avoid or ameliorate neural damage, or in an effort to maintain desired stimulation response(s), or in an effort to avoid undesired stimulation response(s).

The illustrated system for delivering VST is useful in extended therapy applications. Examples of extended therapy applications involve applying stimulation to prevent remodeling of cardiac tissue and to reverse remodel cardiac tissue in cardiovascular disease. VST can be applied for a portion (approximately 10 seconds) of each minute, for example. A VST dose may be adjusted by adjusting the duration or duty cycle of the stimulation (e.g. approximately 5 seconds or 15 seconds each minute or approximately 5 to 15 seconds every 30 seconds or approximately 5 to 30 seconds every 2 minutes, or approximately 5 seconds to 3 minutes every 5 minutes or a continuous stimulation). According to an embodiment, the VST non-selectively stimulates both efferent and afferent axons. The illustrated values are provided by way of example, and not limitation. Over the course of days, weeks, months and years, the physiological response to VST can vary for a number of reasons, such as nerve adaptation, tissue encapsulation, fibrosis, impedance changes, and the like. Various closed loop system embodiments monitor at least one parameter that has a quick and predictable response to VST, and uses the monitored parameter to appropriately change the neural stimulation signal to result in a desired stimulation of the parasympathetic nervous system. Some embodiments monitor heart rate. Some embodiments monitor laryngeal vibrations, and adjust VST intensity as necessary for the VST to elicit laryngeal vibrations. Some open loop VST systems may set the VST intensity to avoid or reduce heart rate effects of VST. For an open loop VST system, heart rate is monitored during VST testing.

Figure 18:
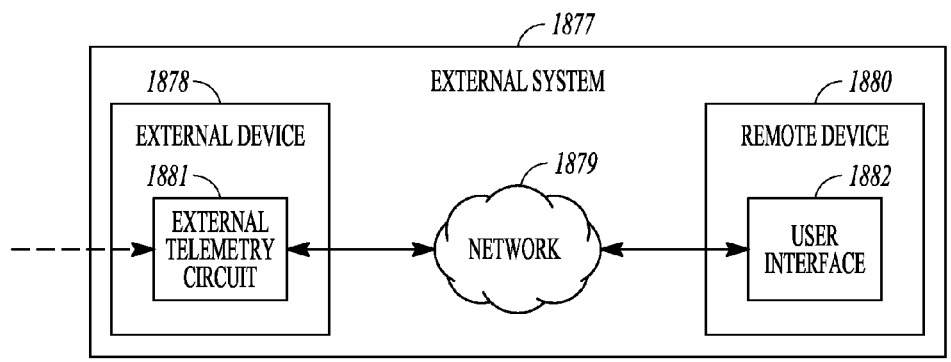
FIG. 18 is a block diagram illustrating, by way of example, an embodiment of an external system.

FIG. 18 is a block diagram illustrating an embodiment of an external system 1877. The external system includes a programmer, in some embodiments. In the illustrated embodiment, the external system includes a patient management system. As illustrated, the external system is a patient management system including an external device 1878, a telecommunication network 1879, and a remote device 1880. The external device 1878 is placed within the vicinity of an implantable medical device (IMD) and includes an external telemetry system 1881 to communicate with the IMD. The remote device(s) is in one or more remote locations and communicates with the external device through the network, thus allowing a physician or other caregiver to monitor and treat a patient from a distant location and/or allowing access to various treatment resources from the one or more remote locations. The illustrated remote device includes a user interface 1882. According to various embodiments, the external device includes a neural stimulator, a programmer or other device such as a computer, a personal data assistant or phone. The external device, in various embodiments, includes two devices adapted to communicate with each other over an appropriate communication channel, such as a computer by way of example and not limitation. The external device can be used to communicate information about a suspected damage to a nerve to the physician and/or to the patient. The external device can be used by the patient or physician to provide feedback indicative of patient discomfort, for example.

Figure 19:
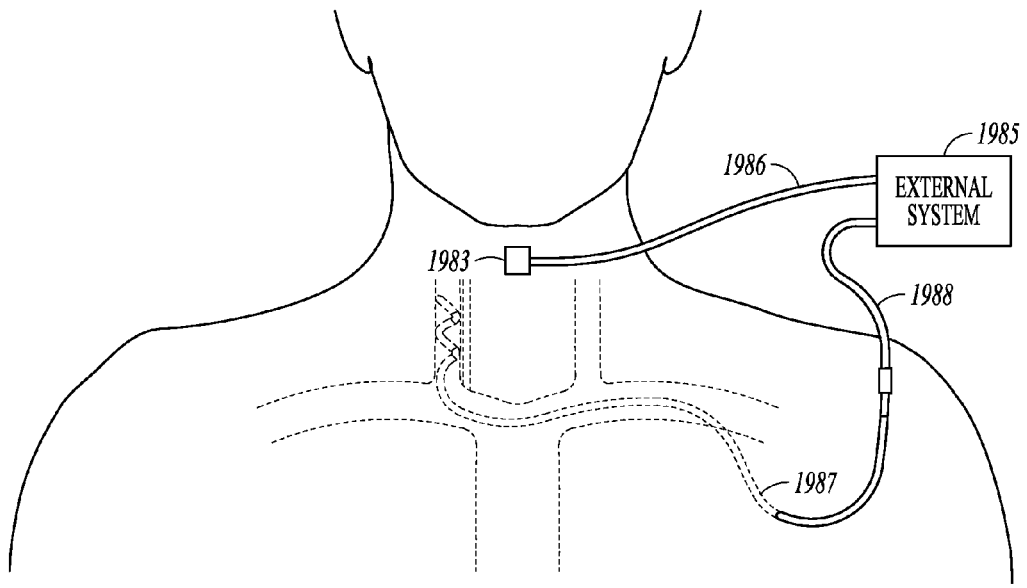
FIG. 19 is an illustration of an embodiment, by way of example, of a neural stimulation system and portions of an environment in which the system is used.

FIG. 19 is an illustration of an embodiment of a neural stimulation system and portions of an environment in which the system is used. The illustrated system includes an activity sensor 1983 for sensing laryngeal activity, a transvenous lead 1984 for delivering vagal nerve stimulation, and an external system 1985 coupled to activity sensor 1983 via a cable 1986 and coupled to lead 1987 via a cable 1988. External system 1985 allows for optimization of the vagal nerve stimulation using the sensed laryngeal activity. The activity sensor 1983 is placed on the neck over the larynx to sense a signal indicative of laryngeal activity. The laryngeal activity is used as a measure of response of vagus nerve to the neural stimulation delivered to vagus nerve. In various embodiments, the laryngeal activity is monitored for placement of stimulation electrodes such as electrodes, optimization of stimulation parameter such as those controlling stimulation intensity (e.g., stimulation amplitude, frequency, duration, and duty cycle), and detection or monitoring of various events that affect the response of vagal nerve 106 to the neural stimulation. The illustrated embodiment may be used to monitor for nerve damage during an implantation procedure.

A number of techniques for sensing laryngeal activity have been previously identified. The techniques include, but are not limited to, accelerometer, EMG and acoustic techniques for detecting laryngeal activity. These techniques may be implemented in an implanted sensor, or may be implemented in an external laryngeal activity sensor, such as is illustrated in FIGS. 19-20.

Figure 20:
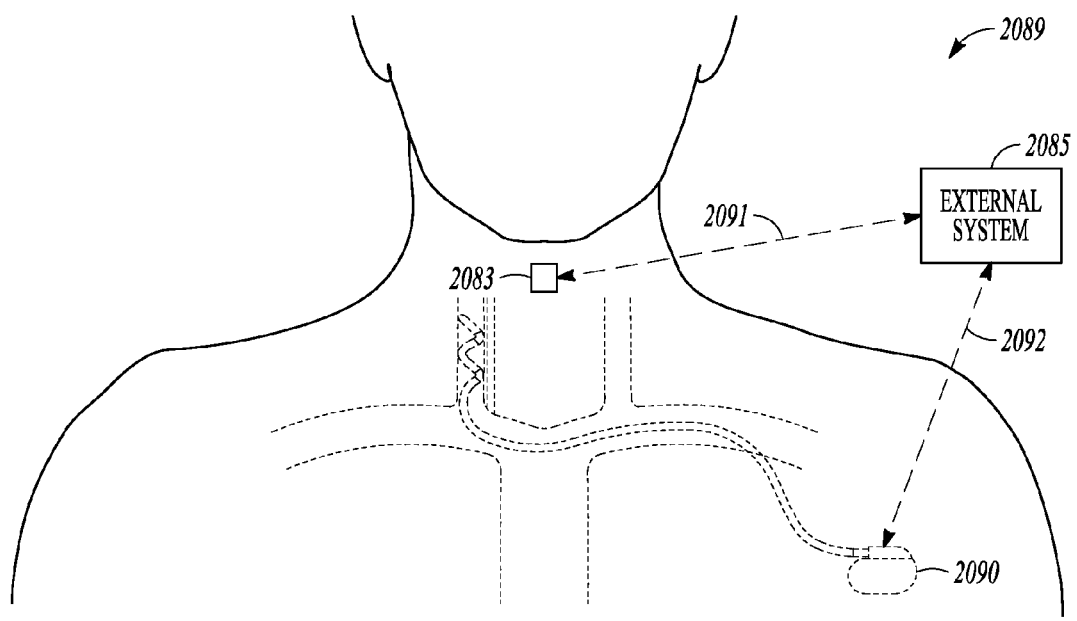
FIG. 20 is an illustration of an embodiment, by way of example, of a neural stimulation system and portions of the environment in which system is used.

FIG. 20 is an illustration of an embodiment of a neural stimulation system and portions of the environment in which system is used. System 2089 differs from system the primarily in that the neural stimulation is delivered from an implantable medical device 2090 implanted in body. In one embodiment, FIGS. 19 and 20 illustrate different stages of implantation and use of an implantable neural stimulation system. FIG. 19 may illustrate a system setup in the middle of an implantation procedure during which lead is inserted with electrodes 116A-B placed to achieve desirable performance of vagal nerve stimulation. FIG. 20 may illustrate the system set-up after the implantable neural stimulation system is fully implanted, such as during the end stage of the implantation procedure when the implantable neural stimulation system is programmed for chronic use or during a follow-up examination during which the implantable neural stimulation system is adjusted if necessary. According to various embodiments, the follow-up examination may be performed by a physician or clinician within a clinical setting. For example, a programmer may review and alert the physician to a drift in the laryngeal threshold as an indicator of potential nerve damage. According to various embodiments, FIG. 20 may illustrate a system used by an ambulatory patient to monitor potential nerve damage, which may further be implemented within a patient management system, such as is illustrated by way of example in FIG. 18.

An illustrated activity sensor 2083 may communicate with an external system 2085 via a wireless link 2091. In some embodiments, the activity sensor 2083 and the external system 2085 are electrically connected using a cable. In another embodiment, the activity sensor 2083 and the external system 2085 are wirelessly coupled through telemetry such as a radio-frequency electromagnetic telemetry link.

In one embodiment, in addition to the neural stimulation circuit, the implantable medical device 2090 includes other monitoring or therapeutic circuits or devices such as one or more of cardiac pacemaker, cardioverter/defibrillator, drug delivery device, and biological therapy device. The external system 2085 provides for control of and communication with implantable medical device 2090 by the user. The external system 2085 and implantable medical device 2090 are communicatively coupled via a telemetry link 2092. In one embodiment, the external system includes a programmer. In another embodiment, the external system is a patient management system including an external device communicating with implantable medical device 2090 via telemetry link 2092, a remote device in a remote location, and a telecommunication network linking the external device and the remote device. The patient management system allows access to implantable medical device 2090 from the remote location, for purposes such as monitoring patient status and adjusting therapies.

FIGS. 19 and 20 illustrate, by way of example, electrodes intravascularly fed into position to transvascularly stimulate the vagus nerve. The present subject matter is not limited to transvascular stimulation of neural targets, as it also may apply to nerve cuffs or other stimulation electrode configurations, and also may apply to other neural targets.

Figure 21:
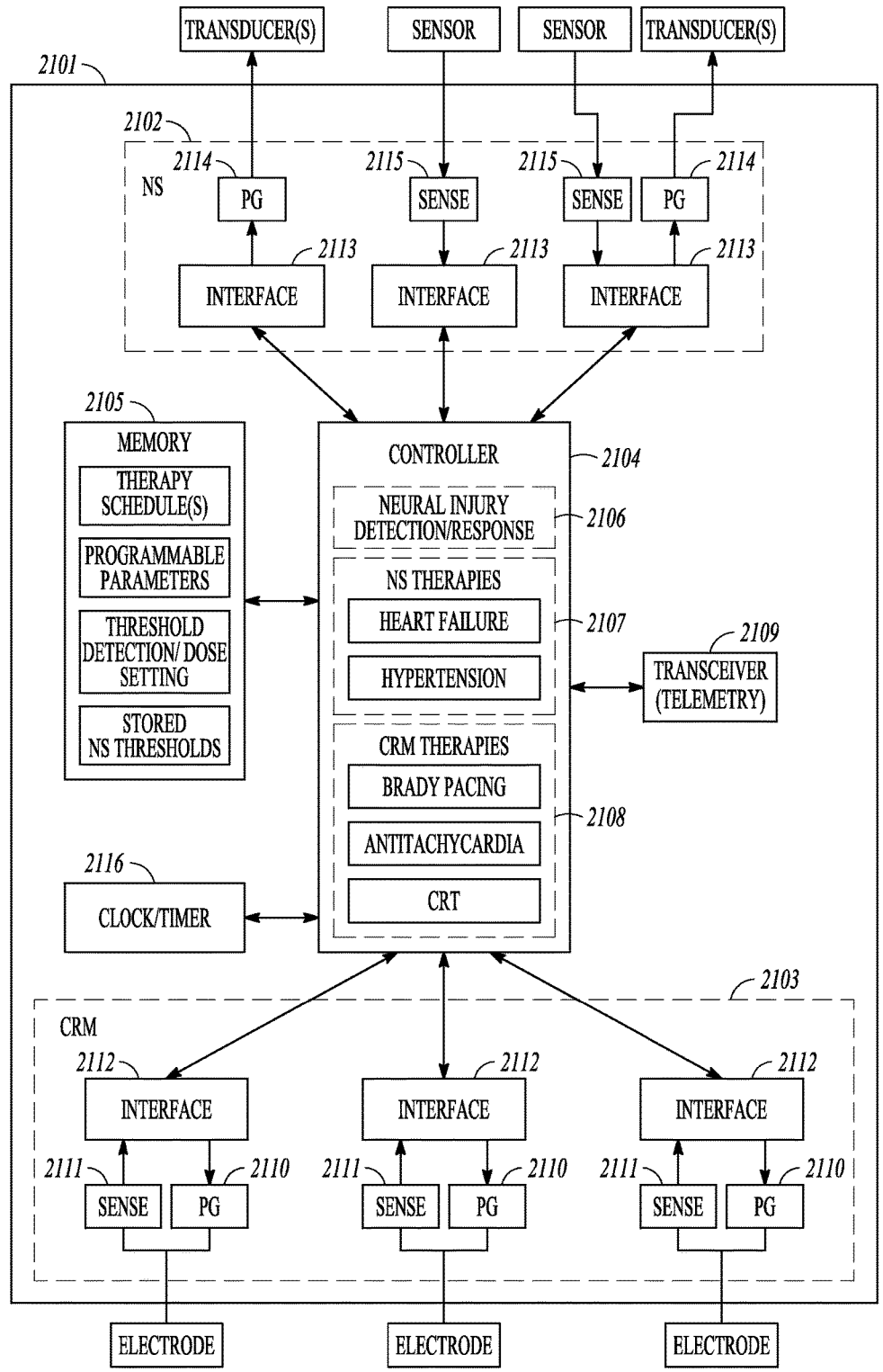
FIG. 21 illustrates, by way of example, an implantable medical device (IMD) having a neural stimulation (NS) component and a cardiac rhythm management (CRM) component according to various embodiments of the present subject matter.

FIG. 21 illustrates an implantable medical device (IMD) 2101 having a neural stimulation (NS) component 2102 and a cardiac rhythm management (CRM) component 2103 according to various embodiments of the present subject matter. The illustrated device includes a controller 2104 and memory 2105. According to various embodiments, the controller includes hardware, software, or a combination of hardware and software to perform the neural stimulation and CRM functions. For example, the programmed therapy applications discussed in this disclosure are capable of being stored as computer-readable instructions embodied in memory and executed by a processor. For example, neural stimulation injury detection routines, therapy schedule(s), programmable parameters and threshold detection or dose setting algorithms such as disclosed herein can be stored in memory. According to various embodiments, the controller includes a processor to execute instructions embedded in memory to perform neural injury detection and response functions 2106, and to perform the neural stimulation 2107 and CRM 2108 functions. The illustrated neural stimulation therapies can include VST, such as VST to treat heart failure, hypertension or other cardiovascular disease. Various embodiments include CRM therapies, such as bradycardia pacing, anti-tachycardia therapies such as ATP, defibrillation and cardioversion, and cardiac resynchronization therapy (CRT). The illustrated device further includes a transceiver 2109 and associated circuitry for use to communicate with a programmer or another external or internal device. Various embodiments include a telemetry coil.

The CRM therapy component 2103 includes components, under the control of the controller, to stimulate a heart and/or sense cardiac signals using one or more electrodes. The illustrated CRM therapy section includes a pulse generator 2110 for use to provide an electrical signal through an electrode to stimulate a heart, and further includes sense circuitry 2111 to detect and process sensed cardiac signals. An interface 2112 is generally illustrated for use to communicate between the controller 2104 and the pulse generator 2110 and sense circuitry 2111. Three electrodes are illustrated as an example for use to provide CRM therapy. However, the present subject matter is not limited to a particular number of electrode sites. Each electrode may include its own pulse generator and sense circuitry. However, the present subject matter is not so limited. The pulse generating and sensing functions can be multiplexed to function with multiple electrodes.

The NS therapy component 2102 includes components, under the control of the controller, to stimulate a neural stimulation target and/or sense parameters associated with nerve activity or surrogates of nerve activity such as heart rate, blood pressure, respiration. Three interfaces 2113 are illustrated for use to provide neural stimulation. However, the present subject matter is not limited to a particular number interfaces, or to any particular stimulating or sensing functions. Pulse generators 2114 are used to provide electrical pulses to transducer/electrode or transducers/electrodes for use to stimulate a neural stimulation target. According to various embodiments, the pulse generator includes circuitry to set, and in some embodiments change, the amplitude of the stimulation pulse, the pulse width of the stimulation pulse, the frequency of the stimulation pulse, the burst frequency of the pulse, and the morphology of the pulse such as a square wave, triangle wave, sinusoidal wave, and waves with desired harmonic components to mimic natural stimulation. Sense circuits 2115 are used to detect and process signals from a sensor, such as a sensor of nerve activity, heart rate, blood pressure, respiration, and the like. Sensor(s) may be used to sense laryngeal vibrations. Sensor(s) may be used to detect a state (e.g. accelerometer used to detect activity). The interfaces 2113 are generally illustrated for use to communicate between the controller 2104 and the pulse generator 2114 and sense circuitry 2115. Each interface, for example, may be used to control a separate lead. Various embodiments of the NS therapy section only include a pulse generator to stimulate a neural target. The illustrated device further includes a clock/timer 2116, which can be used to deliver the programmed therapy according to a programmed stimulation protocol and/or schedule. The illustrated memory 2105 includes therapy schedules, programmable parameters, and threshold detect/dose setting instructions, and further includes storage for include stored neural stimulation threshold.

Figure 22:
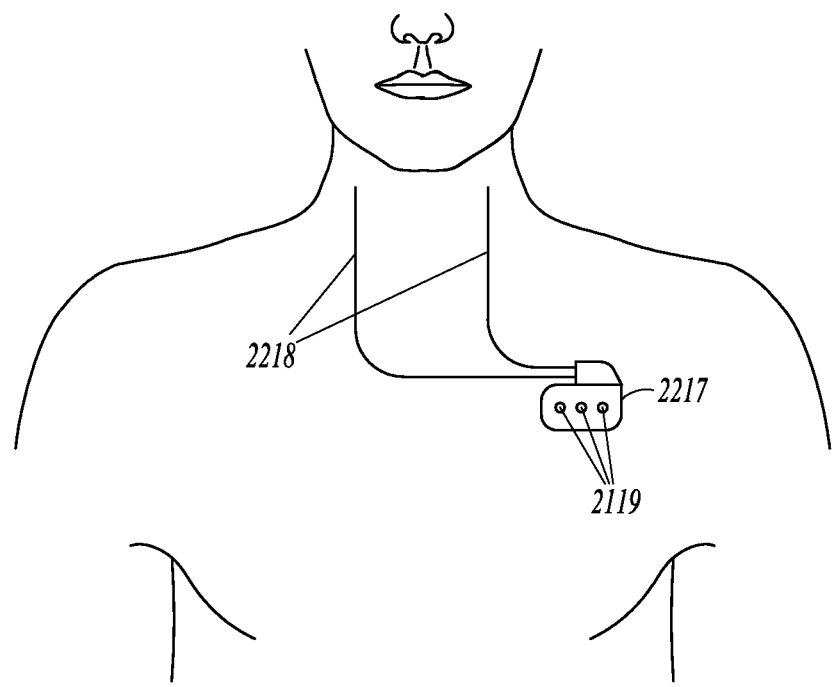
FIG. 22 illustrates, by way of example, a system embodiment in which an IMD is placed subcutaneously or submuscularly in a patient's chest with lead(s) positioned to stimulate a vagus nerve.
Figure 23:
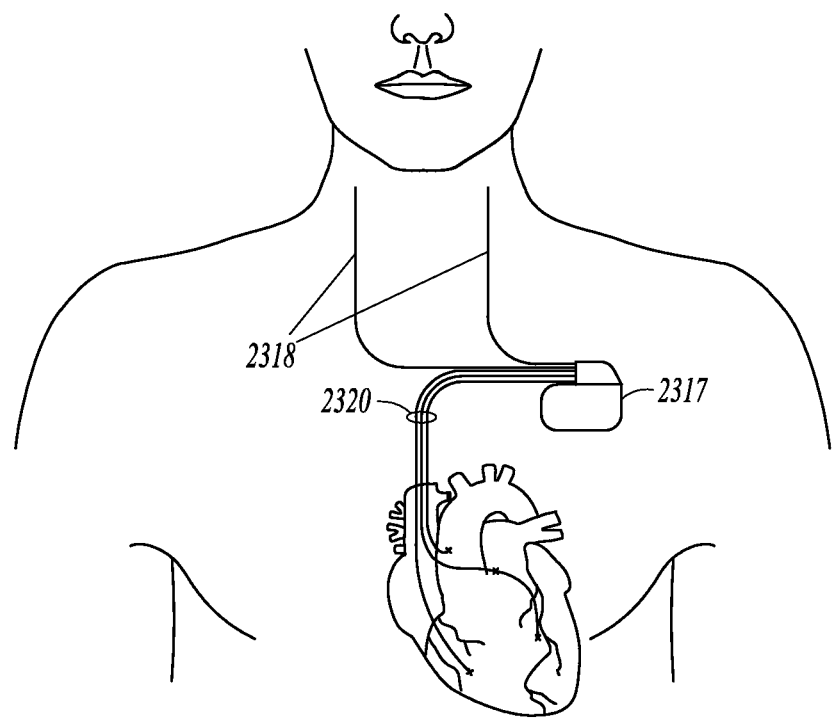
FIG. 23 illustrates, by way of example, an IMD placed subcutaneously or submuscularly in a patient's chest with lead(s) positioned to provide a CRM therapy to a heart, and with lead(s) positioned to stimulate and/or inhibit neural traffic at a neural target, such as a vagus nerve, according to various embodiments.

FIGS. 22-23 illustrate system embodiments adapted to provide VST, and are illustrated as bilateral systems that can stimulate both the left and right vagus nerve. Those of ordinary skill in the art will understand, upon reading and comprehending this disclosure, that systems can be designed to stimulate only the right vagus nerve, systems can be designed to stimulate only the left vagus nerve, and systems can be designed to bilaterally stimulate both the right and left vagus nerves. The systems can be designed to stimulate nerve traffic (providing a parasympathetic response when the vagus is stimulated), or to inhibit nerve traffic (providing a sympathetic response when the vagus is inhibited). Various embodiments deliver unidirectional stimulation or selective stimulation of some of the nerve fibers in the nerve. FIGS. 22-23 illustrate the use of a lead to stimulate the vagus nerve. Wireless technology could be substituted for the leads, such that a leadless electrode is adapted to stimulate a vagus nerve and is further adapted to wirelessly communicate with an implantable system for use in controlling the VST.

FIG. 22 illustrates a system embodiment in which an IMD 2217 is placed subcutaneously or submuscularly in a patient's chest with lead(s) 2218 positioned to stimulate a vagus nerve. According to various embodiments, neural stimulation lead(s) 2218 are subcutaneously tunneled to a neural target, and can have a nerve cuff electrode to stimulate the neural target. Some vagus nerve stimulation lead embodiments are intravascularly fed into a vessel proximate to the neural target, and use electrode(s) within the vessel to transvascularly stimulate the neural target. For example, some embodiments stimulate the vagus using electrode(s) positioned within the internal jugular vein. The neural targets can be stimulated using other energy waveforms, such as ultrasound and light energy waveforms. The illustrated system includes leadless ECG electrodes 2119 on the housing of the device. These ECG electrodes are capable of being used to detect heart rate, for example.

FIG. 23 illustrates an IMD 2317 placed subcutaneously or submuscularly in a patient's chest with lead(s) 2320 positioned to provide a CRM therapy to a heart, and with lead(s) 2318 positioned to stimulate and/or inhibit neural traffic at a neural target, such as a vagus nerve, according to various embodiments. According to various embodiments, neural stimulation lead(s) are subcutaneously tunneled to a neural target, and can have a nerve cuff electrode to stimulate the neural target. Some lead embodiments are intravascularly fed into a vessel proximate to the neural target, and use transducer(s) within the vessel to transvascularly stimulate the neural target. For example, some embodiments target the vagus nerve using electrode(s) positioned within the internal jugular vein.

The present subject matter refers to neural stimulation. Neural stimulation may be delivered in a manner that stimulates neural activity in the target nerve or in a manner that inhibits or blocks neural activity in the target nerve. The present subject matter is applicable to either neural stimulation or inhibition.

The modules and other circuitry shown and described herein can be implemented using software, hardware, firmware and combinations thereof.

The above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. An implantable medical device for implantation in a body and for applying neural stimulation to a neural target in the body, the device comprising:
   a neural stimulation electrode configured for use in stimulating the neural target;
   a neural stimulator configured to deliver neural stimulation through the electrode to the neural target;
   a sensor configured to sense a physiological response to stimulation of motor fibers at the neural target;
   a controller operatively connected to the neural stimulator to control the neural stimulation to deliver a chronic neural stimulation therapy and operatively connected to the sensor to receive a signal indicative of the physiological response; and
   an implantable housing containing the neural stimulator and the controller, wherein the controller is configured to automatically perform a process to detect a potential neural injury where the process includes monitoring the sensed physiological response to detect the potential neural injury and performing an action in response to the detected potential neural injury, wherein in performing the action in response to the detected potential neural injury, the controller is configured to:
      automatically control the neural stimulator to modify the chronic neural stimulation therapy in response to the potential neural injury; or
      automatically control the neural stimulator to suspend the chronic neural stimulation therapy in response to the potential neural injury; or
      automatically initiate a communication signal from the implantable medical device to an external device; or
      automatically store data concerning the detected potential neural injury for later communication.

2. The device of claim 1, wherein the sensor includes an accelerometer configured to sense motion caused by stimulation of motor fibers at the neural target, wherein the controller is configured to monitor the sensed motion to detect the potential neural injury.

3. The device of claim 1, wherein the controller is configured to perform the process to detect the potential neural injury by performing a plurality of neural stimulation threshold tests to monitor for drift in a stimulation threshold stimulating the motor fibers.

4. The device of claim 3, wherein the controller is configured to perform each of the plurality of neural stimulation threshold tests by:
- adjusting an intensity of the neural stimulation across of range of intensity levels;
- for each intensity level, monitoring the signal from the sensor to determine if the neural stimulation causes the physiological response sensed by the sensor; and
- recording, as the neural stimulation threshold; a lowest intensity level for the neural stimulation that causes the motion sensed by the sensor.

5. The device of claim 3, wherein the controller is configured to:
- monitor for acute and chronic changes in the neural stimulation threshold;
- use a first threshold to monitor for acute changes; and
- use a second threshold to monitor for chronic changes.

6. The device of claim 3, wherein the controller is configured to initiate the neural stimulation threshold tests.

7. The device of claim 3, wherein the device includes a programmed schedule, and the controller is configured to initiate the neural stimulation threshold tests according to the programmed schedule.

8. The device of claim 1, wherein the controller is configured to reduce an intensity of the chronic neural stimulation therapy in response to the potential neural injury.

9. The device of claim 8, wherein the controller is configured to:
- reduce an amplitude of the neural stimulation to reduce the intensity of the chronic neural stimulation therapy; or reduce a frequency of the neural stimulation to educe the intensity of the chronic neural stimulation therapy.

10. The device of claim 8, wherein the controller is configured to:
- deliver intermittent neural stimulation with alternating stimulation ON and stimulation OFF times, deliver a train of neural stimulation pulses during the stimulation ON times; and
- reduce a duration of the stimulation ON time to reduce the intensity of the chronic neural stimulation therapy.

11. The device of claim 1, further comprising additional neural stimulation electrodes configured to provide more than one electrode configuration for stimulating the neural target, wherein the controller is configured to stimulate the neural target using a first electrode configuration, and configured to stimulate the neural target using a second electrode configuration in response to the potential neural injury.

12. The device of claim 1, wherein the controller is configured to suspend the chronic neural stimulation therapy for a first period of time to allow for nerve recovery from the potential nerve injury, and then reinitiate delivery of the chronic neural stimulation therapy.

13. The device of claim 12, wherein the controller is configured to:
- redetect the potential neural injury after reinitiating delivery of the chronic neural stimulation therapy; and
- suspend the chronic neural stimulation therapy for a second period of time greater than the first period of time if the potential neural injury is redetected to provide more time for nerve recovery.

14. The device of claim 1, wherein the neural target includes a vagus nerve in a cervical region of the body, and the sensor is configured to detect laryngeal vibration caused by stimulation of motor fibers in the vagus nerve.

15. The device of claim 1, wherein the neural target includes a nerve selected from the group of nerves consisting of:
- a sciatic nerve, a peroneal nerve, a hypoglossal nerve and a spinal motor nerve.

16. The device of claim 1, wherein the controller is configured to check for a device problem to determine if the detected potential injury is likely the device problem rather than an actual neural injury, the controller is configured to check for the device problem in response to the detected potential neural injury before performing the action; and wherein in checking for the device problem, the controller is configured to check lead impedance.

17. An implantable medical device for implantation in a body and for applying neural stimulation to a neural target in the body, the device comprising:
- a neural stimulation electrode configured for use in stimulating the neural target;
- a neural stimulator configured to deliver neural stimulation through the electrode to the neural target;
- a sensor configured to sense a physiological response to stimulation of motor fibers at the neural target;
- a controller operatively connected to the neural stimulator and the sensor; and
- an implantable housing containing the neural stimulator and the controller wherein the controller is configured to control the neural stimulation to deliver a chronic neural stimulation therapy and to implement a process to detect a potential neural injury and perform an action in response to the detected potential neural injury, wherein in performing the action in response to the detected potential neural injury, the controller is configured to:
  - automatically control the neural stimulator to modify the chronic neural stimulation therapy in response to the potential neural injury; or
  - automatically control the neural stimulator to suspend the chronic neural stimulation therapy in response to the potential neural injury; or
  - automatically initiate a communication signal from the implantable medical device to an external device; or
  - automatically store data concerning the detected potential neural injury for later communication.

18. The device of claim 17, wherein the controller is configured to perform the process to detect the potential neural injury by performing a plurality of neural stimulation threshold tests to monitor for drift in a stimulation threshold stimulating the motor fibers.

19. The device of claim 18, wherein the controller is configured to initiate the neural stimulation threshold tests.

20. The device of claim 18, wherein the device includes a programmed schedule, and the controller is configured to initiate the neural stimulation threshold tests according to the programmed schedule.

* * * * *